United States Patent
Boyd et al.

(10) Patent No.: US 6,599,709 B1
(45) Date of Patent: *Jul. 29, 2003

(54) METHOD FOR SCREENING FOR SOLUBLE LIGANDS TO A RECEPTOR-TYPE TYROSINE KINASE

(75) Inventors: Andrew W. Boyd, Ascot Vale (AU); Richard Simpson, Richmond (AU); Ian Wicks, Kew (AU); Larry David Ward, Balaclava (AU); David Wilkinson, West Brunswick (AU)

(73) Assignee: The Walter and Eliza Hall Institute of Medical Research, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 09/442,649

(22) Filed: Nov. 18, 1999

Related U.S. Application Data

(63) Continuation of application No. 08/715,106, filed on Sep. 18, 1996, now Pat. No. 6,020,306, which is a continuation of application No. 08/167,919, filed on Apr. 18, 1994, now Pat. No. 5,674,691.

(30) Foreign Application Priority Data

Jun. 21, 1991 (AU) .......................................... PK6841/91
Dec. 12, 1991 (AU) .......................................... PK9992/91

(51) Int. Cl.$^7$ .......................... G01N 33/53; C12N 9/12; A61K 38/00
(52) U.S. Cl. ....................... 435/7.2; 435/7.1; 435/7.21; 435/7.8; 435/7.92; 435/194; 514/2; 514/12
(58) Field of Search ....................... 514/2, 12; 435/194, 435/7.21, 7.8, 70.3, 7.92, 7.1, 7.2

(56) References Cited

U.S. PATENT DOCUMENTS

| | | |
|---|---|---|
| 5,447,860 A | 9/1995 | Ziegler |
| 5,457,048 A | 10/1995 | Pasquale et al. |
| 5,512,457 A | 4/1996 | Lyman et al. |
| 5,674,691 A * | 10/1997 | Boyd et al. .................. 435/7.2 |

FOREIGN PATENT DOCUMENTS

WO 91/05288 2/1992

OTHER PUBLICATIONS

Reeck, et al. (Aug. 28, 1987) "'Homology' in Proteins and Nucleic Acids: A Terminology Muddle and a Way Out of it" *Cell* 50:667.

Cantley, et al. (Jan. 25, 1991) "Oncogenes and Signal Transduction" *Cell* 64:281–302.

Lhotak, et al. (May 1991) Accession No. p54762, database, SWISS–PROT34.

MacPherson, B. in Radionuclides in Clinical Chemistry, Howard et al. (eds) 1980, chapter 6, pp. 77–90, Little, Brown and Company, USA.

Hirai, et al. (Dec. 1987) "A Novel Putative Tyrosine Kinase Receptor Encoded by the eph Gene" *Science* 238:1717–1720.

Lhotak, et al. (May 1991) "Characterization of Elk, A Brain–Specific Receptor Tyrosine Kinase" *Molecular and Cellular Biology* 11:2496–2502.

Lindberg, et al. (Dec. 1990) "cDNA Cloning and Characterization of eck, An Epithelial Cell Receptor Protein–Tyrosine Kinase in the eph/elk Family of Protein Kinases" *Molecular and Cellular Biology* 10(12):6316–6324.

Pasquale (Jul. 1991) "Identification of Chicken Embryo Kinase 5, A Developmentally Regulated Receptor–Type Tyrosine Kinase of the Eph Family" *Cell Regulation* 2:523–534.

Sajjadi, et al. (Aug. 1991) "identified of a New eph–Related Receptor Tyrosine Kinase Gene from Mouse and Chicken that is Developmentally Regulated and Encodes at Least Two Forms of the Receptor" *The New Biologist* 3(8):769–778.

Flanagan, et al. (Oct. 5, 1990) "The Kit Ligand: A Cell Surface Molecule Altered in Steel Mutant Fibroblasts" *Cell* 63:185–194.

* cited by examiner

Primary Examiner—Gary Kunz
Assistant Examiner—Jegatheesan Seharaseyon
(74) Attorney, Agent, or Firm—Scully, Scott, Murphy & Presser

(57) ABSTRACT

The present invention relates to a method of screening for ligands to a receptor-type tyrosine kinase. The receptor-type tyrosine, in its naturally occurring form, is characterized by being reactive to monoclonal antibody III.A4, having an apparent molecular weight of approximately 120–150 kD in its glycosylated form, and having the N-terminal amino acid sequence E L I P Q P.

5 Claims, 24 Drawing Sheets

Figure 1:
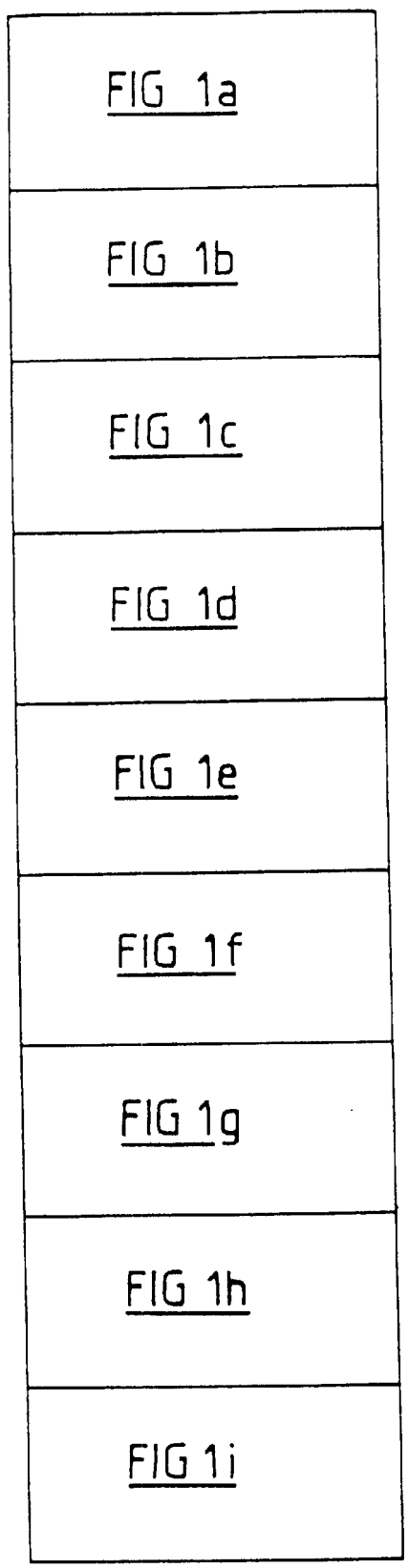

```
                                                                                           *
CATGGATGGTAACTTCTCCAGCAATCAGAGGCGCTCCCCCTCACATCAGTGGCATGCTTCATGGA

1.
                                       M  D  C
GATATGCTCCTCACTGCCCTCTGCACCAGCAAC ATGGATTGT                                           108
 Q  L  S  I  L  L  L  L  S  C  S  V  L  D  S  F  G  E  L  I  P
                10                                   20
CAGCTCTCCATCCTCCTCCTTCTCAGCTGTTCTGTTCTCGACAGTTTCGGG GAACTGATTCCGC
--------------------------------------------------
 Q  P  S  N  E  V  N  L  L  D  S  K  T  I  Q
AGCCTTCCAATGAAGTCAATCTACTGGATTCAAAACAATTCAA                                           216
                                            30
 G  E  L  G  W  I  S  Y  P  S  H  G  W  E  E  I  S  G  V  D  E
 40                                   50                           60
GGGGAGCTGGGCTGGATCTCTTATCCATCACATGGGTGGGAAGAGATCAGTGGTGTGGATGAAC
 H  Y  T  P  I  R  T  Y  Q  V  C  N  V  M  D
                                          70
ATTACACACCCATCAGGACTTACCAGGTGTGCAATGTCATGGAC                                          324
                                             80                         90
 H  S  Q  N  W  L  R  T  N  W  V  P  R  N  S  A  Q  K  I  Y
CACAGTCAAAACAATTGGCTGAGAACAAACTGGGTCCCCAGGAACTCAGCTCAGAAGATTTATG
```

FIG 1a

```
        100           110
V E L K F  F T L R D C N S  I P L
TGGAGCTCAAGTTCACTCTACGAGACTGCAATAGCATTCCATTG           540

120                    130
V L G T C K E  F T F N L Y Y M E S D D D H G
GTTTTAGGAACTTGCAAGGAGACATTCAACCTGTACTACATGGAGTCTGATGATGATCATGGGG

140
V K F R E H Q F T K I D T I A
TGAAATTCGAGAGCATCAGTTTACAAAGATTGACACCATTGCA           648

150                      160
A D E S F T Q M D L G D R  I L K L N T E  I
GCTGATGAAAGTTCACTCAAATGGATCTTGGGAGACCGTATTCTGAAGCTCAACACTGAGATTA 170                   180
R E V G P V N K K G F Y L A F
GAGAAGTAGGTCCTGTCAACAAGAAGGGATTTTATTTGGCATTT           756

190                   200
Q D V G A C V A L V S V R V Y F K K C P F
CAAGATGTTGGTGCTTGCGTCCTTGGTGTCTGTGAGAGTATACTTCAAAAAGTGCCCATTTA

210
T V K N L A M F P D T V P M D
CAGTGAAGAATCTGGCTATGTTTCCAGACACGGTACCCATGGAC
```

FIG 1b

```
220                   230        ▶
  S   Q   S   L   V   E   V   R   G   S   C   V   N   N   S   K   E   E   D   P   P
TCCCAGTCCCCTGGTGGAGGTTAGAGGGTCTTGTGTCAACAATTCTAAGGAGGAAGATCCTCCAA              864

250
  R   M   Y   C   S   T   E   G   E   W   L   V   P   I   G
GGATGTACTGCAGTACACAGAAGGCGAATGGCTTGTACCCATTGGC 260                    270
  K   C   S   C   N   A   G   Y   E   E   R   G   F   M   C   Q   A   C   R   P   G
AAGTGTTCCTGCAATGCTGGCTATGAAGAAAGAGGTTTTATGTGCCAAGCTTGTGACCAGGTT 280                    290
  F   Y   K   A   L   D   G   N   M   K   C   A   K   C   P
TCTACAAGGCATTGGATGGTAATATGAAGTGTGCTAAGTGCCCG                                    972

300
  P   H   S   S   T   Q   E   D   G   S   M   N   C   R   C   E   N   N   Y   F   R
CCTCACAGTTCTACTCAGGAAGATGGTTCAATGAACTGCAGGTGTGAGAATAATTACTTCCGGG

320
  A   D   K   D   P   P   S   M   A   C   T   R   P   P   S          ▶
CAGACAAAGACCCTCCATCCATGGCTTGTACCCGACCTCCATCT                                   1080

330                                  ▶
  S   P   R   N   V   I   S   N   I   N   E   T   S   V   I   L   D   W   S   W   P
TCACCAAGAAATGTTATCTCTAATATAAACGAGACCTCAGTTATCCTGGACTGGAGTTGGCCCC
```

FIG 1c

```
       350         D  T  G  G  R  K  D  V  T  F  N  I  I  C
        L  D
TGGACACAGGAGGCCGGAAAGATGTTACCTTCAACATCATATGT                                    1188
                                      380
                                       V  R  F  L  P
 K  K  C  G  W  N  I  K  Q  C  E  P  C  S  P  N
AAAAAATGTGGGTGGAATATAAACAGTGTGAGCCATGCAGCCCAAATGTCCGCTTCCTCCCTC                 1296
                   ▶
                ▶  N  T  T  V  T  V  T  D  L
 R  Q  F  G  L  T
GACAGTTTGGACTCACCAACACCGGTGACAGTGACAGACCTT
                ▶                      420
       400      ▶                       S
        L  A  H  T  N  Y  T  F  E  I  D  A  V  N  G  V  S  E  L  S
CTGGCACATACTAACTACACCTTTGAGATTGATGCCGTTAATGGGGTGTCAGAGCTGAGCTCCC
                             430
 P  P  R  Q  F  A  A  V  S  I  T  T  N  Q  A
CACCAAGACAGTTTGCTGCGGTCAGCATCACAACTAATCAGGCT                                    1404
                        440               450
                         V  L  T  I   K  D  R  T  S  R  N  S  I  S  L  S
 A  P  S  P
GCTCCATCACCTGTCCTGACGATTAAGAAAGATCGGACCTCCAGAAATAGCATCTCTTTGTCCT
            460                 470
 W  Q  E  P  E  H  P  N  G  I  I  L  D  Y  E
GGCAAGAACCTGAACATCCTAATGGGATCATATATTGGACTACGAG                                  1512

FIG 1d
```

```
         V  K  Y  Y  E  K  Q  F  Q  E  T  S  Y  T  I  L  R  A  R  G  T
                                480              490
         GTCAAATACTATGAAAAGCAGGAATTCAAGAAACAAGTTATACCATTCTGAGGGCAAGAGGCACAA  1620
                    ▶        N  V  T  I  S  S  L  K  P  D  T  I  Y  V  F
                             500
         ATGTTACCATCAGTAGCCTCAAGCCTGACACTATATACGTATTA
                    ▶        510
         Q  I  R  A  R  T  A  A  G  Y  G  T  N  S  R  K  F  E  F  E  T
                             520
         CAAATCCGAGCCCGAACAGCCGCTGGATATGGGACGAACAGCCGCAAGTTTGAGTTTGAAACTA
         S  P  D  S  F  S  I  S  G  E  S  S  Q  V  V
         530                          540
         GTCCAGAGACTCTTTTCTCCATCTCTGGTGAAAGTAGCCAA GTGGTC                       1728

M  I  A  I  S  A  A  V  A  I  L  L  T  V  V  I  Y  V  L  I
                   550                              560
         ATGATCGCCATTTCAGCGGCAGTAGCAATTATTCTCACTGTTGTCATCTATGTTTGATTG

G  R  F  C  G  Y  K  ;  K  H  G  A  D  E  K
                        570
         GGAGGTTCTGTGGCTATAAGTCAAAAACATGGGGCAGATGAAAAA
         R  L  H  F  G  N  G  H  L  K  L  P  G  L  R  T  Y  V  D  P  H
         580                                      590                     600
         AGACTTCATTTTGGCAATGGGCATTTAAAACTTCCAGGTCTCAGGACTTATGTTGACCCACATA      1836
```

FIG 1e

```
         T  Y  E  D  P  T  Q  A  V  H  E  F  A  K  E
                              610
        CATATGAAGACCCTACCCAAGCTGTTCATGAGTTTGCCAAGGAA                           1944

L  D  A  T  N  I  S  I  D  K  V  V  G  A  G  E  F  G  E  V  C
                    620                                    •     •  •
        TTGGATGCCACCAACATATCCATTGATAAAGTTGTTGGAGCAGGTGAATTTGGAGAGGTGTGCA       2052
                                          650
         S  G  R  L  K  L  P  S  K  K  E  I  S  V  A
                640
        GTGGTCGCTTAAAACTTCCTTCAAAAAGAGATTTCAGTGGCC

I  K  T  L  K  V  G  Y  T  E  K  Q  R  R  D  F  L  G  E  A  S
                              660                                  670
        ATTAAAACCCTGAAAGTTGGCTACACAGAAAAGCAGAGAGACTTCCTGGGAGAAGCAAGCA          2160

I  M  G  Q  F  D  H  P  N  I  I  R  L  E  G
                              680
        TTATGGGACAGTTTGACCACCCCAATATCATTCGACTGGAAGGA

V  V  T  K  S  K  P  V  M  I  V  T  E  Y  M  E  N  G  S  L  D
                690                                  700
        GTTGTTACCAAAAGTAAGCCAGTTATGATTGTCACAGAATACATGGAGAATGGTTCCTTGGATA      2268

S  F  L  R  K  H  D  A  Q  F  T  V  I  Q  L
           710                            720
        GTTTCCTACGTAAACACGATGCCCAGTTTACTGTCATTCAGCTA
```

FIG 1f

```
V  G  M  L  R  G  I  A  S  G  M  K  Y  L  S  D  M  G  Y  V  H
                  730                    740
CTGGGGATGCTTCGAGGGATAGCATCTGGCATGAAGTACCTGTCAGACATGGGCTATGTTCACC    2376

R  D  L  A  A  R  N  I  L  I  N  S  N  L  V
            750
GAGACCTCGCTGCTCGGAACATCTTGATCAACAGTAACTTGGTG

C  K  V  S  D  E  G  L  S  R  V  L  E  D  D  P  E  A  A  ◆ Y
760                          770
TGTAAGGTTTCTGATTTCGGACTTTCGCGTGTCCTGGAGGATGACCCAGAAGCTGCTTATACAA    2484

T  R  G  G  K  I  P  I  R  W  T  S  P  E  A
CAAGAGGAGGAAGATCCCAATCAGGTGGACATCAGGTGGACATCACCAGAAGCT

I  A  Y  R  K  F  T  S  A  S  D  V  W  S  Y  G  I  V  L  W  E
      800                                  810
ATAGCCTACCGCAAGTTCACGTCAGCCAGCGATGTATGGAGTTATGGGATTGTTCTCTGGGAGG

V  W  S  Y  G  E  R  P  Y  W  E  M  S  N  Q
      820                          830
TGATGTCTTATGGAGAGAGACCATACTGGGAGATGTCCAATCAG                        2592

D  V  I  K  A  V  D  E  G  Y  R  L  P  P  P  M  D  C  P  A  A
GATGTAATTAAAGCTGTAGATGAGGGCTATCGACTGCCACCCCCCATGGACTGCCCAGCTGCCT
```

FIG 1g

```
              861
L  Y  Q  L  M  L  D  C  W  Q  K  D  R  N  N
TGTATCAGCTGATGCTGGACTGCTGGCAGAAAGACAGGAACAAC                              2700
                   870                 880
R  P  K  F  E  Q  I  V  S  I  L  D  K  L  I  R  N  P  G  S  L
AGACCCAAGTTTGAGCAGATTGTTAGTATTCTGGACAAGCTTATCCGGAATCCCGGCAGCCTGA
       890                 900
K  I  I  T  S  A  A  A  R  P  S  N  L  L  L
AGATCATCACCAGTGCAGCCGCAAGGCCATCAAACCTTCTTCTG                              2808
                   910                 920
D  Q  S  N  V  D  I  S  T  F  R  T  T  G  D  W  L  N  G  V  R
GACCAAAGCAATGTGGATATCTCTACCTTCCGCACAACAGGTGACTGGCTTAATGGTGTCCGGA
       930                              960
T  A  H  C  K  E  I  F  T  G  V  E  Y  S  S                           G
CAGCACACTGCAAGGAAATCTTCACGGGCGTGGAGTACAGTTCT                              2916
940                             950
C  D  T  I  A  K  I  S  T  D  D  M  K  K  V  G  V  T  V  V  G
TGTGACACAATAGCCAAGATTTCCACAGATGACATGAAAAAGGTTGGTGTCACCGTGGTTGGGC
                   970
P  Q  K  K  I  I  S  S  I  K  A  L  E  T  Q
CACAGAAGAAGATCATCAGTAGCATTAAAGCTCTAGAAACGCAA                              3024
```

FIG 1h

```
              980
 S  K  N  G  P  V  P  V  *                                                   3132
TCAAAGAATGGCCCAGTTCCCGTGTAAAGCACGACGGAAGTGCTTCTGGACGGAAGTGGTGGCT
GTGGAAGGCGTCAAGTCATCCTGCAGACAGACAATAATTCTGGA
```

FIG 1i

HEK  ..MDCQLSILLLLSCSVLDSFGELIPQPSNEVNLLDSTKIQGELGWISYPSHGWEEISGVDE

ELK  MAL--...L--F-LA-AVAAME-.........T-M-TR-ATA----TAN-AS----V--Y--

HEK  TFNLYYMESDDDHGVK.....FREHQFTKIDTIAADESFTQMDLGDRILKLNTEIREVGPVNK

ELK  ------Y-T-SVIAT-KSAFWS-APYL-V--------S-V-F-G-LM-V---V-SF--LTR

HEK  SKEEDPP.RMYCSTEGEWLVPIGKCSCNAGYE.ERGFMCQACRPGFYKALDGNMKCAKCPPH

ELK  AE-V-V-IKL--NGD---M----R-T-K----P-NSVA-K--PA-TF--SQEAEG-SH--GN

FIG 2a

```
HYTPIRTYQVCNVMDHSQNNWLRTNWVPRNSAQKIYVELKFTLRDCNSIPLVLGTCKE    118
NLNT------------FEPN------L-TFIN-RG-HR--T-MR---V---S-L-N-P-S----  108

KGFYLAFQDVGACVALVSVRVYFKKCPFTVKNLAMFPDTV.PMDSQSLVEVRGSCVNN   233
N------------Y----MS-L------F-----SI-Q-F-V--E-MTGAE-T---IA--T-IP-  228

SSTQEDGSMNCRCENNYFRADKDPPSMACTRPPSSPRNVISNINETSVILDWSWPLDT   351
-RSPSEA-PI-T-RTG-Y----F---EV---SV--G------IV-----I--E-HP-RE-   348
```

FIG 2b

HEK  GGRKDVTFNIICKKCGWNIKQCEPCSPNVRFLPRQFGLTNTTVTDLLAHTNYTFEIDAVN

ELK  ---D----Y------RADRRS-SR-DD--E-V---L--ECR-SISS-W---P---D--Q--I-

HEK  VKYYEKQEQETSYTILRARGTNVTISSLKPDTIYVFQIRARTAAGYGTNSRKFEFETSPDSFSI

ELK  IR----EHN-FNSSMA-SQTNTAR-DG-R-GMV--V-V---V----KF-G-MC-Q--LT-DDYK

HEK  LPGLRTYVDPHTYEDPTOAVHEFAKELDATNISIDKVVGAGEEGEVCSGRLKLPSKKEISVA

ELK  .--MKI-I--F-----NE---R-----I--VSFVK--EE-I------YK-----G-R--Y---

FIG 2c

```
GVSELSSPPRQFAAVSITTNQAAPSPVLTIKKDRTSRNSISLSWQEPEHPNGIILDYE    471
----SK-PF-P-HVS-N--------T-PIMHQVSATMR--T---PQ--Q---------    468

SGESSQVVMIAISAAVAIILLT..VVIYVLIGRFCGYKSKHGADEKRLHFGNGHLK     589
-ELRE-LPL--G----AGVVFVVSL-A-SIVCS-KRA-SKEAVYSD-LQ-YST-RGS    588

IKTLKVGYTEKQRRDFLGEASIMGQFDHPNIIRLEGVVTKSKPVMIVTEYMENGSLDS   709
-----A--S------S-----------------R---I--F----A---           707
```

FIG 2d

```
HEK  FLRKHDAQFTVIQLVGMLRGIASGMKYLSDMGYVHRDLAARNILINSNLVCKVSDFGLSRVLEDD.
ELK  ---QN-G-----------------A-------E-N-------------V-------------Y-Q--T

HEK  MSNQDVIKAVDEGYRLPPPMDCPAALYQLMLDCWQKDRNNRPKFEEQIVSILDKLIRNPGS
ELK  ------N-IEQD---------------H-----------------S--R-AE--NT----M----A-

HEK  TDDMKKVGVTVVGPQKKIISSIKALETQSKNGPVPV*
ELK  SE-LLRI---LA-H-----L---HSMRV-MNQS-SVMA*
```

FIG 2e

PEAAYTTR.GGKIPIRWTSPEAIAYRKFTSASDVWSYGIVLWEVMSYGERPYWE 827

SDPT---SSL-----V----A----------------M-----F------D 827

LKIITSAAARPSNLLLDQSNVDISTFRTTGDWLNGVRTAHCKEIFTGVEYSSCDTIAKIS 947

--TVATIT-V--QP---R-IP-FTA-T-VD---SAIKMVQYRDS-LTAGFT-LQLVTQMT 947

FIG 2f

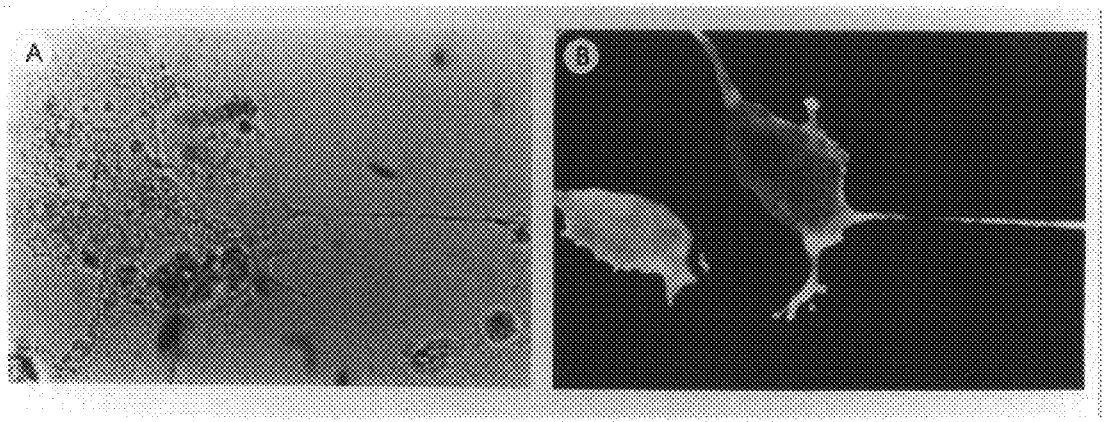
FIG.3A                    FIG.3B

FIG 8
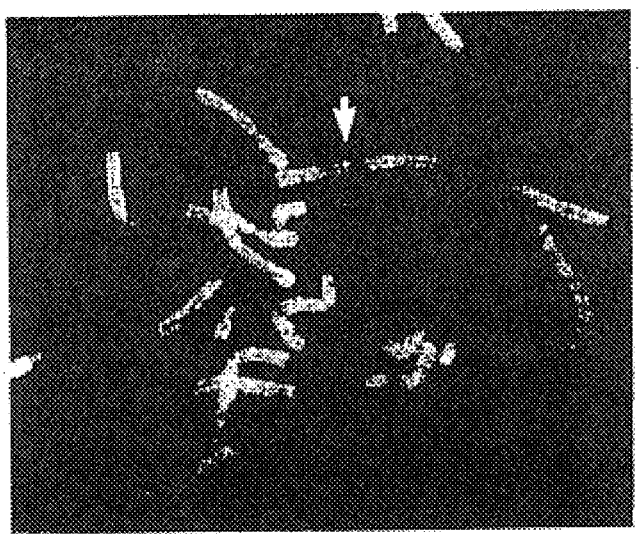

METHOD FOR SCREENING FOR SOLUBLE LIGANDS TO A RECEPTOR-TYPE TYROSINE KINASE

CROSS REFERENCE TO RELATED APPLICATION

The present application is a continuation of application Ser. No. 08/715,106, filed on Sep. 18, 1996, which is a continuation of application Ser. No. 08/167,919, filed on Apr. 18, 1994, which issued as U.S. Pat. No. 5,674,691, on Oct. 7, 1997.

The present invention relates generally to a novel receptor-type tyrosine kinase and to genetic sequences encoding same.

Tyrosine kinases form an important class of molecules involved in the regulation of growth and differentiation (1). One mode of proof for this role came from the identification of receptors which bind known soluble growth factors. The receptors for epidermal growth factor (EGF) (2), platelet derived growth factor (PDGF) (3) and colony stimulating factor-1 (CSF-1)(4) were all shown to be transmembrane molecules with the cytoplasmic regions encoding a tyrosine kinase catalytic domain. The CSF-1 receptor is homologous to the PDGF receptor in both the catalytic and extracellular domains (1,5). The extra cellular domain of these proteins is distinguished from other tyrosine kinases by the presence of immnunoglobulin-like repeats (1,6). Based on structural properties of the kinase domain, the c-kit protein was identified as another member of this family (7). The c-kit gene locus appears to underpin the defects in the congenitally anaemic W/W mouse (8–10). The ligand has now been identified (11–14) as shown to be encoded by the Sl locus. The locus is abnormal in the Steel mouse (15) which has identical defects to the W/W mouse but encodes a normal c-kit gene.

The other line of evidence for a critical role of tyrosine kinase proteins in growth control came from the study of viral oncogenes (16–17). These genes were shown to be directly involved in growth dysregulation by observations of a change in cell growth following introduction of DNA encoding these genes into fibroblasts. AU oncogenes have been shown to have close cellular homologues (proto-oncogenes). One of the first identified oncogenes was v-src, the cellular homologue (c-src) is the prototypical representative of the family of cytoplasmic tyrosine kinases which, following myristylation, become associated with the inner leaf of the cell membrane (18). Within the haemopoletic system a number of lineage-restricted src-like kinases have been defined (19).

The T cell-associated src-like kinase, lck, has been shown to associate independently with both the CD4 and CD8 transmembrane glycoproteins to form a signalling complex (20,21). By contrast, v-erb-B and v-fms, like their cellular homologues the EGF receptor and CSF 1 receptor, respectively, are transmembrane molecules encoding the entire signal transduction machinery in a single polypeptide (1,17).

Detailed analysis of the amino acid sequences of these proteins has revealed conserved structural motifs within the catalytic domains (5). Both tyrosine and serine-thereonine kinases have a consensus GXGXXG sequence (SEQ ID NO: 12) which is found in many nucleotide binding proteins (5). Other conserved sequence motifs are shared by both types of kinase while others are specific for the tyrosine or the threonine-serine kinase subgroups (5). The tyrosine kinases, while having regions of sequence conservation specific to this family, can be further subdivided according to the structural features of the regions 5' to the catalytic domain (1,4–7). The novel tyrosine kinase of the present invention exhibits the same general characteristics as previously known tyrosine kinases.

In accordance with the present invention, a new receptor-type tyrosine kinase is provided and which is identified as a member of the eph/elk family of tyrosine kinases (22,23). The novel tyrosine kinase receptor is designated HEK ("human eph/elk-like kinase"). As the present inventors have identified expression of HEK in both pre-B and T cell lines, the receptor molecule of the present invention and/or its ligand is contemplated herein to have particular applicability for use as agents in the in vivo modulation of the production and/or function of pre-B, B and T cells.

Accordingly, one aspect of the present invention provides an isolated receptor-type tyrosine kinase, said tyrosine kinase characterised by, in its naturally occurring form, being reactive to the monoclonal antibody III.A4, having an apparent molecular weight of approximately 120–150 kD in the glycosylated form and having an N-terminal amino acid sequence comprising:

E L I P Q P (SEQ ID NO: 1).

Preferably, the tyrosine kinase has an N-terminal amino acid sequence comprising:

(E L I P Q P S N E V N L X D (SEQ ID NO: 2), wherein X is any amino acid and is preferably L.

More preferably, the tyrosine kinase has an N-terminal amino acid sequence comprising the amino acids:

E L I P Q P S N E V N L X D (S) K X$^1$ I Q U (SEQ ID NO:3), wherein X and X$^1$ are any amino acid and preferably L and T, respectively.

Even more preferably, the tyrosine kinase comprises the amino acid sequence set forth in FIG. 1 or any parts or portions thereof, or having an amino acid sequence with at least 30% homology to the amino acid sequence set forth in FIG. 1 and having the identifying characteristics of HEK. More preferably, the degree of homology is at least 40%, still more preferably at least 55, even more preferably at least 70% and still even more preferably greater than 80%.

The hybridoma producing the monoclonal antibody III.A4 was deposited at Public Health Laboratory Service, European Collection of Animal Cell Cultures, Porton Down Salisbury, UK, on Jun. 20, 1991 under accession number 91061920.

The term "isolated" as used in relation to the tyrosine kinase of the present invention includes a biologically pure preparation comprising at least 20%, preferably at least 40%, more preferably at least 60% and even more preferably at least 80% of the protein relative to other molecules as determined by weight, activity or other convenient means. The term also encompasses any form of the protein not in the naturally occurring state such as, but not limited to, a preparation of membranes containing the protein, a preparation of the protein separate from the membrane or a supernatant fluid comprising said protein. The preparation may be glycosylated, partially unglycosylated or complete unglycosylated or may have a glycosylation pattern altered from what is naturally occurring.

The tyrosine kinase of the present invention is expressed on a number of tumours of human origin. In particular, data are presented herein showing HEK expression in human lymphoid tumour cell lines LK63, Lila-1, JM, MOLT4 and HSB-2 and the human epithelial tumour HeLa. One skilled in the art, however, will immediately recognise that similar or homologous kinases may exist on non-tumour cells or on non-human tumours and which have similar properties to the tyrosine kinase of the present invention. For example, the results contained herein show some expression of HEK in heart muscle. Accordingly, the present invention extends to a tyrosine kinase functionally and structurally similar in any or all respects to the tyrosine kinase herein described including a kinase of non-tumour origin.

The present invention extends to preparations comprising the naturally occurring form of the tyrosine kinase protein, including any naturally occurring derivative forms thereof, as well as to synthetic and recombinant forms of the protein including any single or multiple amino acid substitutions, deletions and/or insertions to the polypeptide portion of the kinase and to analogues and homologues thereof. Such amino acid alterations to the molecule are examples of recombinant or synthetic mutants and derivatives of the kinase.

Insertions include amino acid and/or carboxyl terminal fusions as weU as intra-sequence insertions of single or multiple amino acids. Generally, insertions within the amino acid sequence will be smaller than amino or carboxyl terminal fusions, of the order of say 1 to 4 residues. Insertional amino acid sequence variants are those in which one or more amino acid residues are introduced into a predetermined site in the protein. Deletional variants are characterised by the removal of one or more amino acids from the sequence. Substitutional variants are those in which at least one residue in the sequence has been removed and a different residue inserted in its place. Such subsitutions generally are made in accordance with the following Table 1.

TABLE 1

| Original Residue | Exemplary Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Generally amino acids are replaced by other amino acids having like properties, such as hydrophobicity, hydrophilicity, electronegativity, bulky side chains, etc.

Amino acid substitutions are typically of single residues; insertions usually will be on the order of about 1–10 amino acid residues; and deletions will range from about 1–20 residues. Deletions or insertions preferably are made in adjacent pairs, i.e: a deletion of 2 residues or insertion of 2 residues.

The amino acid variants referred to above may readily be made using peptide synthetic techniques well known in the art, such as solid phase peptide synthesis (Merrifield; J. Am. Chem. Soc., 85: p2149, 1964) and the like, or by recombinant DNA manipulations. Techniques for making substitution mutations at predetermined sites in DNA having known sequence are weU known, for example M13 mutagenesis. The manipulation of DNA sequences to produce variant proteins which manifest as substitutional, insertional or deletional variants are well known in the art and are described for example in Maniatis et al (Molecular Cloning: A Laboratory Manual; Cold Spring Harbor Laboratory, 1982).

Other examples of recombinant or synthetic mutants and derivatives of the tyrosine kinase protein of this invention include single or multiple substitutions, deletions and/or additions to any molecule associated with the kinase such as carbohydrates, lipids and/or proteins or polypeptides. Furthermore, it is possible that the tyrosine kinase protein of the present invention is a genetically altered version of a similar protein on normal cells. The present invention, therefore, extends to the ryrosine kinase protein from tumour or non-tumour origin and to all genetically altered forms thereof.

The terms "analogues" and "derivatives" extend to any functional chemical equivalent of the tyrosine kinase protein characterised by its increased stability and/or efficacy in vivo or in vitro. The terms "analogue" and "derivatives" also extend to any amino acid derivative of the ryrosine kinase protein as described above.

Analogues of HEK contemplated herein include, but are not limited to, modifications to side chains, incorporation of unnatural amino acids and/or derivatising the molecule and the use of crosslinkers and other methods which impose conformational constraints on the peptides or their analogues. Examples of side chain modifications contemplated by the present invention include modifications of amino groups such as by reductive alkylation by reaction with an aldehyde followed by reduction with NaBH4; amidination with methylacetimidate; acylation with acetic anhydride; carbamoylation of amino groups with cyanate; trinitrobenzylation of amino groups with 2, 4, 6 trinitrobenzene sulphonic acid (TNBS); acylation of amino groups with succinic anhydride and tetrahydrophthalic anhydride; and pyridbxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbomoylation with cyanate at alkaline pH.

Tryptophan residues may be modified by, for example, oxidation with N-bromosuccinimide or alkylation of the indole ring with 2-hyroxy-5-nitrobenzyl bromide or sulphenyl halides. Tyrosine residues on the other hand, may be altered by nitration with tetranitromethane to form a 3-nitrotyrosine derivative.

Modification of the imidaxole ring of a histidine residue may be accomplished by alkylation with jodoacetic acid derivatives or N-carbethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bufinctional reagents which usually contain an amino-reactive moiety such as N-hydroxysuccinimide and another group specificreactive moiety such as maleimido or dithio moiety (SH) or carbodiimide (COOH). In addition, peptides could be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention, therefore, extends to peptides or polypeptides and amino acid and/or chemical analogues thereof having the identifying characteristics of HEK as broadly described herein, and/or to regions thereof capable of, or responsible for, its action in transducing signals or in stimulating cellular responses such as growth and/or differentiation.

Accordingly, reference herein to the receptor-type tyrosine kinase of the present invention includes the naturally occurring molecule, recombinant, synthetic and analogue forms thereof and to any mutants, derivatives and human and non-human homologues thereof. All such kinases are encompassed by the term "HEK".

The present invention further extends to the ligand for the novel receptor-type tyrosine kinase described herein and to any agonists and antagonists (e.g. soluble form of the receptor) of the enzyme. Since the tyrosine kinase is an oncogenic protein, antagonists to the receptor are of particular relevance and fall within the scope of the present invention. Such antagonists include antibodies (monoclonal and polyclonal), the enzyme itself in soluble form or otherwise, specific peptides, polypeptides or proteins and carbohydrates, amongst others. These types of antagonists are useful in developing anti-tumour agents where the growth or maintenance of the tumour itself is supported by the tyrosine kinase of the present invention. Accordingly, the addition of an effective amount of an antagonist to the tumour-associated receptor-type tyrosine kinase will inhibit, reduce or otherwise interfere with the receptor activity of the protein and thus prevent, reduce and/or inhibit tumour growth. The present invention, therefore, extends to pharmaceutical compositions comprising one or more antagonists to the tyrosine kinase herein described and one or more pharmaceutically acceptable carriers and/or diluents.

Ligand(s) for HEK are capable of being screened for in a number of ways. In one protocol, an expression vector (e.g. AP-TAG-HEK) is selected which encodes the entire extracellular region of HEK fused to an appropriate reporter molecule like alkaline phosphatase. The fusion protein expressed in cells is recovered from cell supernatants and used to stain (using the reporter molecule) tissue sections using the methods as described by Flanagan and Leder (39), the disclosure of which is incorporated herein by reference.

Once cellular sources of ligand are identified these cells are then used to construct an expression library. If the ligand is cell bound (eg membrane bound), the expression vector (eg. AP-TAG-HEK) is used to stain pools to search for positive clones. If the HEK ligand is secreted, then another strategy will be required. In this case, supernatants of pools can be used to screen for induction of HEK phosphorylation in LK63 or HEK transfectants. Alternatively, supernatants from tissues producing HEK ligand can be used as a source in affinity purification on columns to which the product of, for example, pEE14-HEK is linked as a specific absorbent. The sequence of the purified ligand will be determined and this information used to clone the HEK ligand from cDNA libraries.

Another aspect of the present invention is directed to a nucleic acid isolate comprising a sequence of nucleotides encoding the novel receptor-type tyrosine kinase (including its recombinant, synthetic, mutant, derivative, analogue and homologue forms). The nucleic acid sequence may comprise deoxyribonucleotides or ribonucleotides and may exst in single or double stranded form, alone or in combination with a vector or expression vector molecule. The nucleic acid may be naturally occurring RNA or DNA or may be cDNA including complementary forms thereof. The nucleic acid molecule may also contain single or multiple nucleotide substitutions, deletions and/or additions relative to the nucleotide sequence encoding the naturally occurring or recombinant form of the protein. The vectors containing the nucleic acid sequences of the present invention may replicate in eukaryotes and/or prokaryotes and contain promoter sequences capable of expression in one or both of these types of cells. Suitable cells include mammalian, insect, yeast and/or bacterial cells. Particularly preferred cell types include CHO, baculovirus and *E. coli* cells. The preferred nucleotide sequence comprising HEK is set forth in FIG. 1. The general techniques of recombinant DNA technology, including isolation of recombinant proteins, are well known and are described for example in Maniatis et al (Supra).

This invention also provides a transgenic cell or cell culture carrying a nucleic acid isolate as described above.

In another aspect, this invention provides a pharmaceutical composition comprising a soluble form of the receptor-type tyrosine kinase as broadly described herein, said composition further comprising one or more pharmaceutically acceptable carriers and/or diluents.

This invention also extends to methods of use of the novel receptor-type tyrosine kinase of this invention and of antagonists to ligands binding to this tyrosine kinase.

In one aspect, this invention extends to a method of ameliorating the effects of interaction or binding between HEK and its ligand in a mammal comprising administering to said mammal an effective amount of the antagonist to a ligand binding to the tyrosine kinase of this invention.

The invention also extends to a method of phosphorylating a protein comprising contacting a preparation of said protein with an effective amount of the receptor-type tyrosine kinase of this invention for a time and under conditions sufficient to effect phosphorylation of the protein.

In yet another aspect, the invention provides a method of screening for a ligand bound to tissue or cells to the receptor-type tyrosine kinase of this invention comprising contacting the tyrosine kinase fused to a reporter molecule capable of producing a detectable signal to the tissue or cell sample to be tested for a time and under conditions sufficient for the fused tyrosine kinase to bind to a ligand on said tissue or cells and then detecting the reporter molecule.

The invention further provides a method of screening for a soluble ligand to the receptor-type tyrosine kinase of this invention comprising contacting a sample to be tested with a cell line capable of expressing the tyrosine kinase and screening for phosphorylation in said cell line.

One skilled in the art will, however, irtediately recognise that a variety of mutations, derivatives or chemical alternations can be made to the sequence to encode, for example, the analogues and derivatives disclosed above. The present invention also extends to short nucleic acid molecules which can act as nucleic acid probes to screen for the presence of the HEK gene or mutations therein.

The present invention is further described with reference to the following non-limiting Figures and Examples.

In the Figures:

FIG. 1 is a representation showing nucleotide sequence (SEQ ID NO: 9) and deduced amino acid sequence (SEQ ID NO: 10) of HEK coding sequence with partial 3' and 5' untranslated sequence. Numbers at right indicate positions of nucleotides and numbers above amino acids refer to amino acid sequence. A single underline indicates the presumed signal peptide. Double underline indicates the presumed transmembrane region. Dashed overline indicates identity between the predicted amino acid sequence and the sequence obtained from purified HEK protein. Triangles indicate potential sites for N-linked glycosylation within the extra-cellular domain. Dots indicate the putative ATP-binding site. The diamond indicates a putative autophosphorylation site. Asterisks indicate stop codons.

Figure 2:
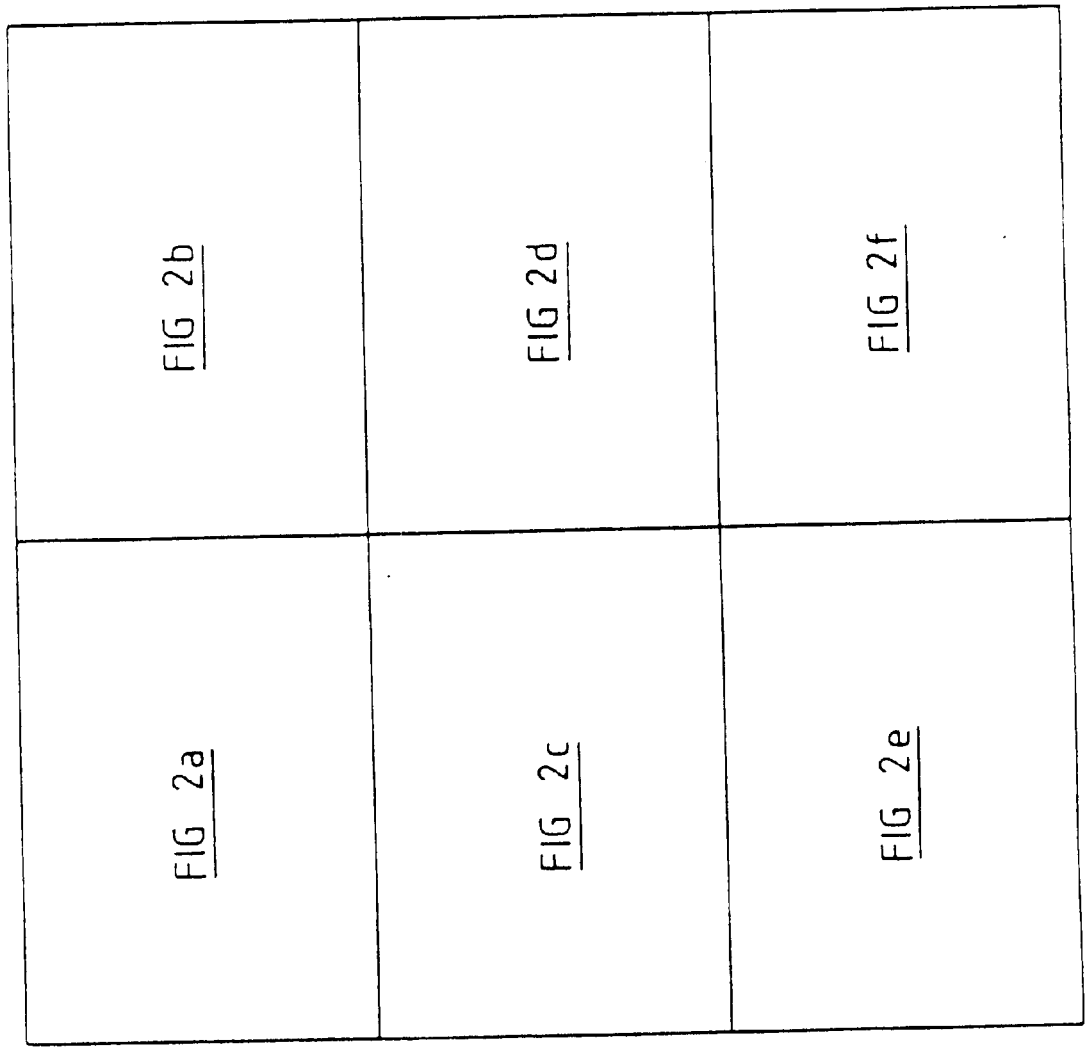

FIG. 2 is a representation showing protein sequence alignment of HEK with elk (SEQ ID NO: 11), a related gene within the eph/elk family. Alignment was performed using the GAP programme. Amino acid positions are numbered on the right. Dots in the sequence indicate gaps introduced to optimize the alignment. Dashes indicate identity between amino acids. Asterisks indicate stop codons. Dots above the line of amino acids indicates residues contributing to the two repeats of homology with fibronectin type III, within the C-terminal regions of the extracellular domains. Triangles above the line of amino acids highlight conserved cyseine residues within the N-terminal region.

FIG. 3 is a photographic representation showing expression of HEK in COS cells. The HEK 4.5 kb cDNA clone was subcloned into the expression vector CDM8. COS cells were transfected with this construct using DEAE-dextran/chloroquine and DMSO. Two days after transfection cells were stained in situ with the III.A4 MAb followed by FITC-conjugated sheep anti-mouse Ig and photographed under light microscopy (panel A), or fluorescence microscopy (panel B). Magnification ×400.

Figure 4:
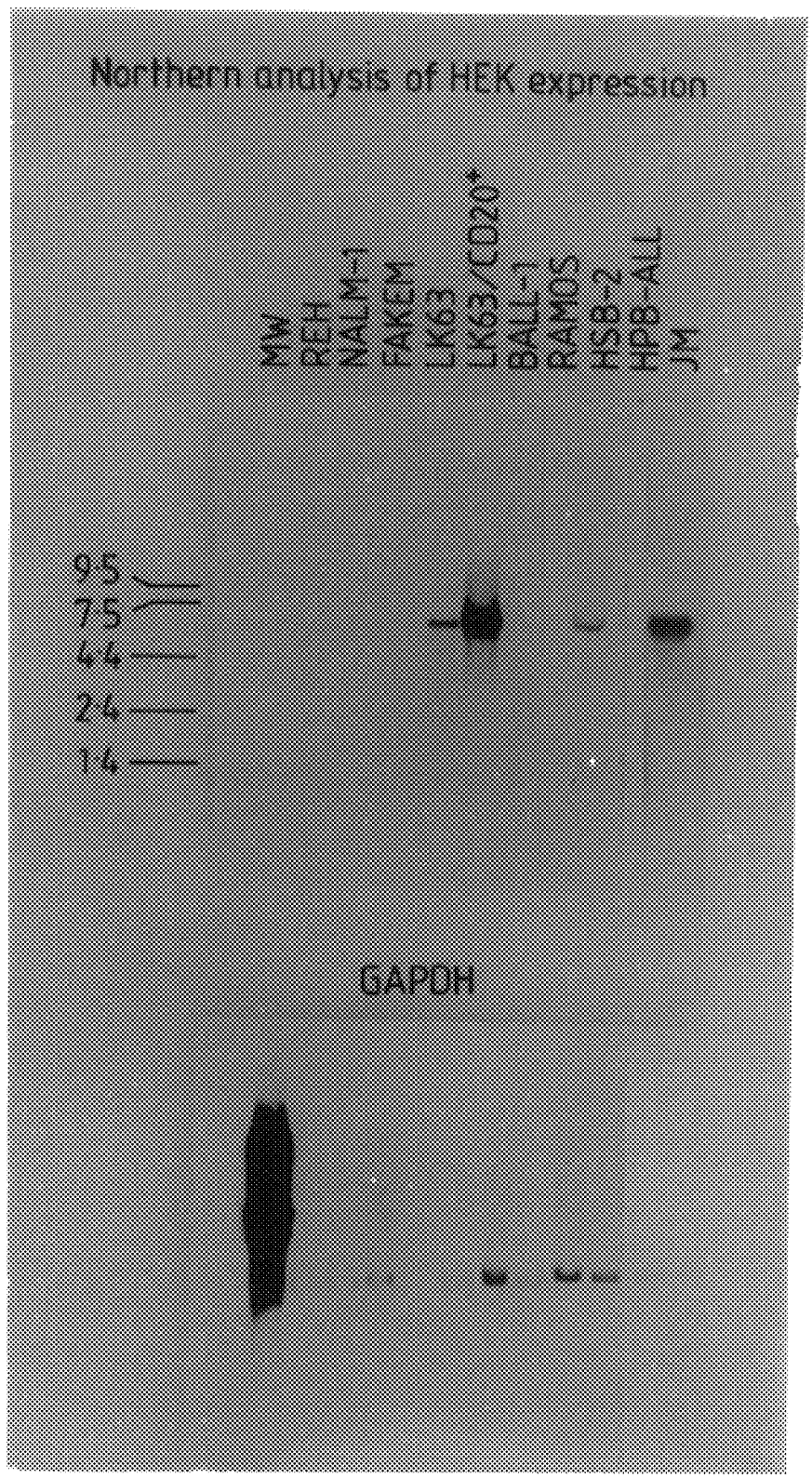

FIG. 4 is a photographic representation of Northern blot analysis of HEK expression in cell lines. Poly (A)+RNA from human cell lines was fractionated on an agarose/formaldehyde gel and transferred onto Hybond-C extra membrane. The filter was hybridised with the HEK 4.5 kb cDNA (upper panel). The same filter was hybridised with GAPDH as a quantitative control (lower panel), REH, NALM-1 and FAYEM are pre-B leukaemic cell lines. BALL-1 is an early B leukaemic cell line. RAMOS is a mature B leukaemic cell fine. HSB-2, HPB-ALL and JM are T leukaemic cell lines.

Figure 5:
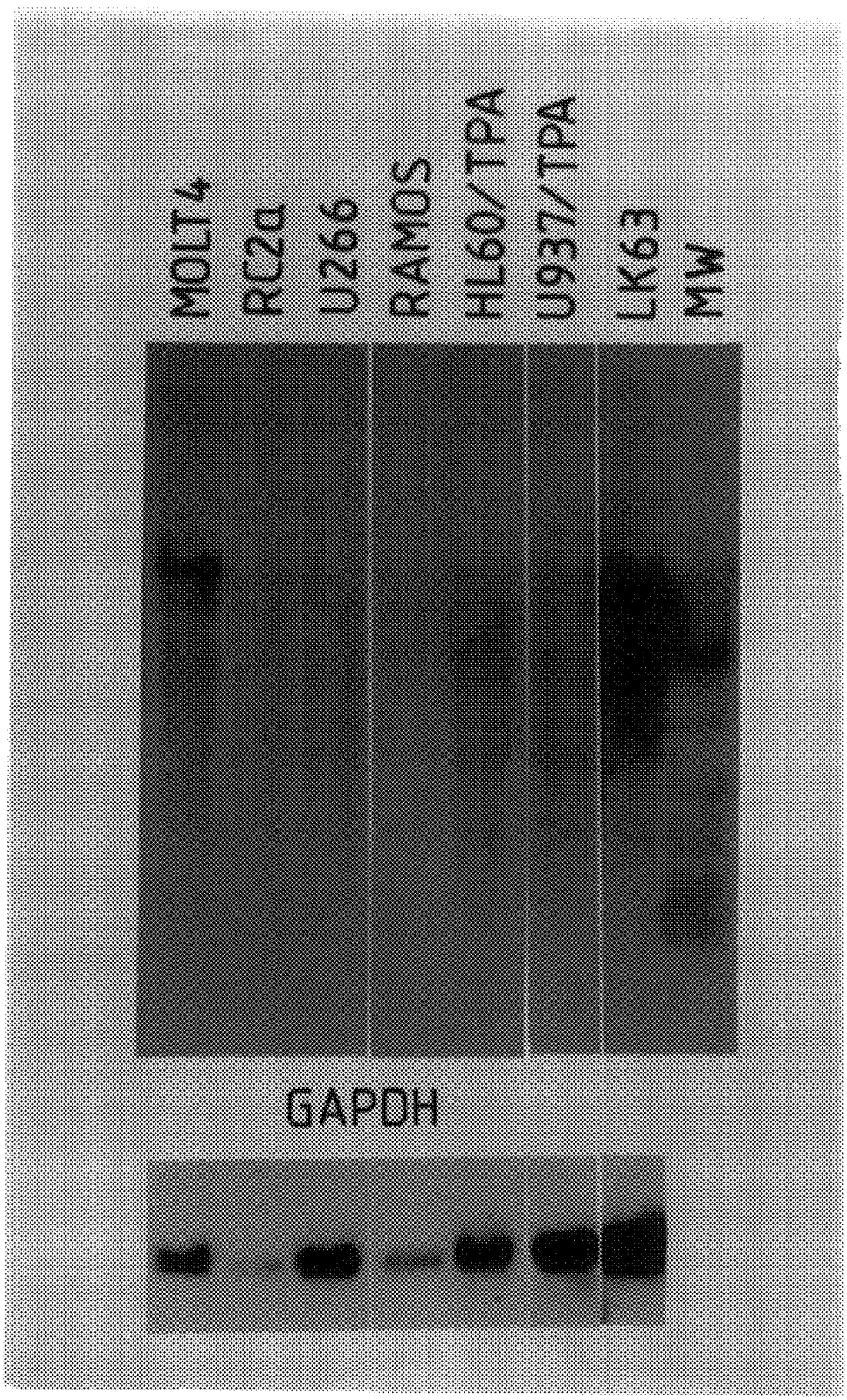

FIG. 5 is a photographic representation showing Northern blot analysis of HEK expression in cell lines. Poly A$^+$ RNA from human cell lines was probed for HEK expression as above. Molt 4 is an immature T cell line. RC2a, HL60 and U937 are myelomonocytic cell lines. In this experiment, RNA was extracted from HL60 and U937 after treatment of cels with tetra decannoyl phorbol myristic acetate (TPA), an activator of protein kinase C. U266 is a mature B cell line.

Figure 6:
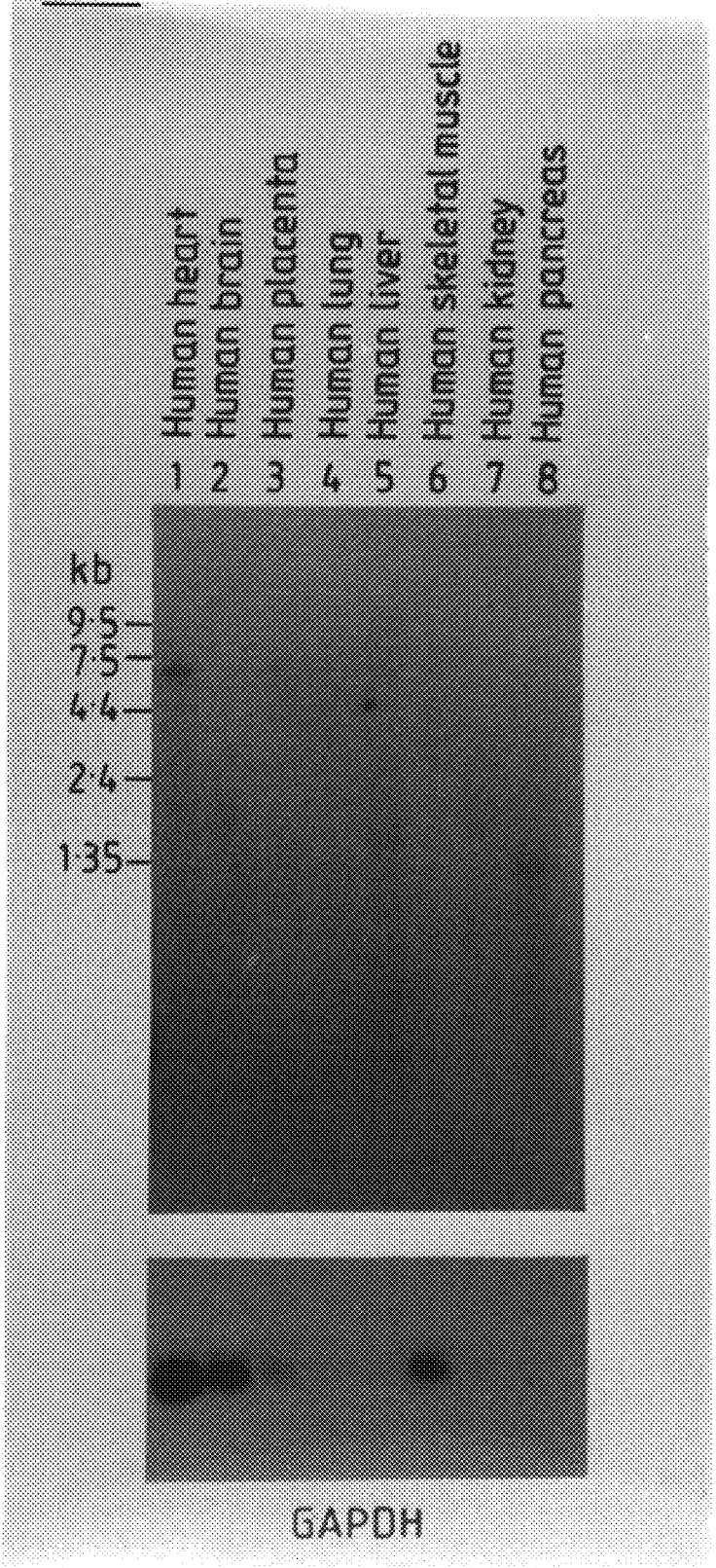

FIG. 6 is a photographic representation showing Northern analysis of HEK expression in adult post mortem tissues. A multiple tissue Northern blot was purchased commercially and probed for HEK expression under conditions suggested by the manufactuerer (Clontech). The 1.3 kb band in pancreas is too small to represent a transcript for a secreted form of HEK and is probably due to cross hybridisation.

Figure 7:
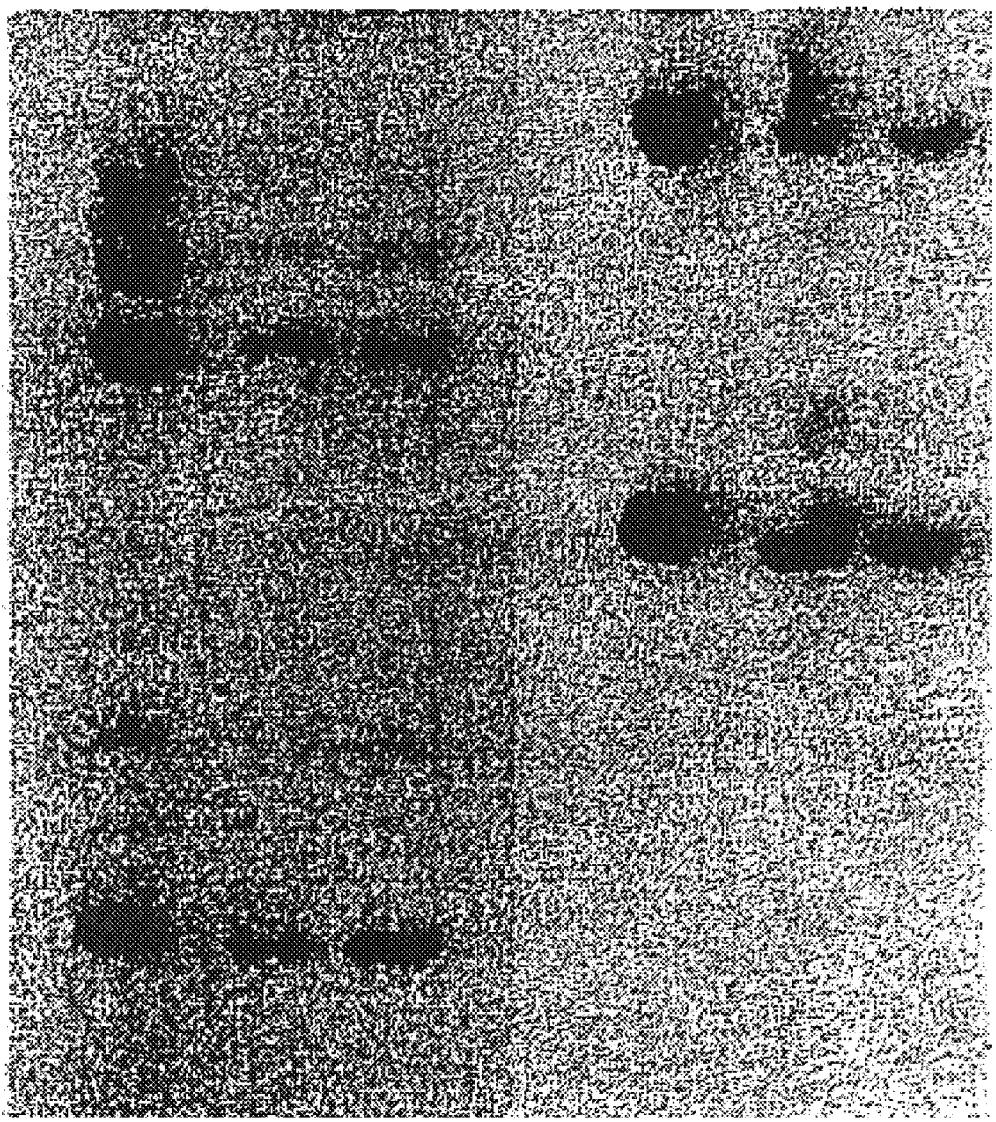

FIG. 7 is a photographic representation showing Southern blot analysis of HEK in cell lines and normal human peripheral blood cell DNA. Samples were digested with Hind III (lanes 1–3) or Bam HI (lanes 4–6), run on a 1% agarose gel and transferred to Zetaprobe membrane. The membrane was hybridised with a 1.1 kb fragment of HEK, extending from nucleotides 1,109 to 2,241 (see FIG. 1). Lanes 1 and 4, normal peripheral blood; Lanes 2 and 5, LK63 cells; lanes 3 and 6, LK63/CD20+ cells.

FIG. 8 is a photographic representation showing in situ hybridisation. The ~1.1 kb HEK PCR product referred to above was nick translated with biotin-14-dATP and hybridised in situ at a probe concentration of 5 ng/$\mu$l to metaphases from two normal males. Chromosomes were stained before analysis with both propidium iodide (as counterstain) and DAPI (for chromosome identification).

Figure 9:
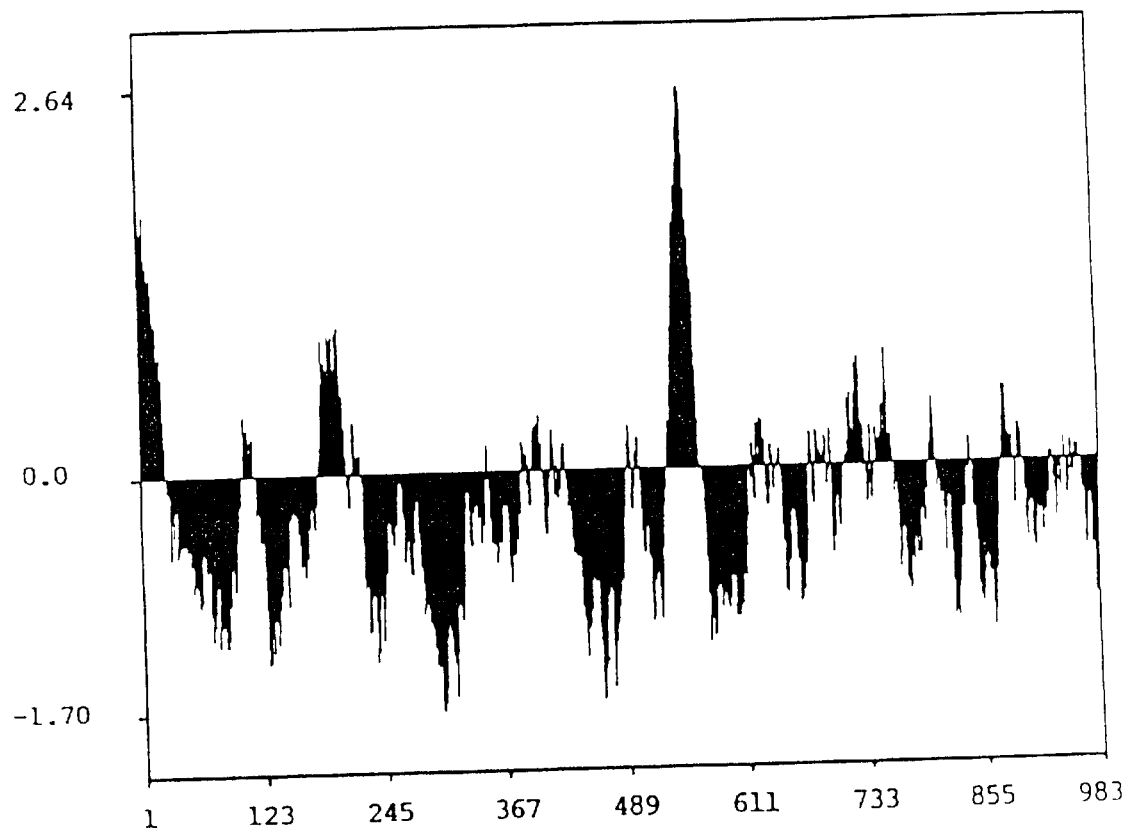

FIG. 9 is a graphical representation showing a hydropathy analysis (span length: 25) of the predicted translational product of the HEK 4.5 cDNA. The Y axis indicates a hydropathy index, with hydrophobic residues appearing above the origin and hydrophilic residues below. The AAs comprising the translated product of the HEK cDNA are numbered along the X axis from 1–983.

EXAMPLE

1. Materials and Methods

Cell Lines, Mab III4 HEK Protein Structure and Function

The LK63 and LK63/CD20+ cell lines were derived from a child with acute lymphoblastic leukaemia. LK63/CD20+ is a tetraploid variant of LK63, which arose spontaneously in vitro and has enhanced HEK expression. In contrast to the parental cell line, LK63/CD20+ expresses CD20. These lines have cytogenetic features of pre-B cell leukaemia and have not been transformed with Epstein-Barr virus (24). JM and HSB-2 are CD8+, human T cell leukaemic cell lines.

The IIIA4 Mab was generated against the LK63 cell line and recognised a 135 kD, cell surface molecule (HEK) with in vitro kinase activity expressed by LK63, LK63/CD20+ and JM (25).

The IIIA4 Mab was used to purify HEK antigen for amino acid sequencing (25). The amino acid sequences obtained were as follows, where doubtful residues are bracketed and unidentified residues are marked X: N terminus-ELIPQPSNEVNLXD(S)KXIQ (SEQ ID NO: 3); internal-GYRLPPPMDCPAALYQLMLDC (SEQ ID NO: 4).

LK63 cDNA Library Construction and Screening

A random primed cDNA library was constructed in λgt10 (Amersham) using 5 ug of poly A+ selected mRNA from LK63/CD20+ cells. A degenerate oligonucleotide was designed on the basis of the internal (3') HEK protein sequence. The neutral base inosine was included at positions of high codon degeneracy (26). The 51 mer:

(SEQ ID NO: 5)
```
TACCGICTICCICCICCIATGGACTGCCCIGCIGCICTITACCAACTIATG
    T              T T           T   G
``` was end labeled using γ32P-deoxyadenosine triphosphate (ATP) and polynucleotide kinase, followed by separation on a G25 Sephadex column as previously described (27). Approximately 250,000 plaques were screened in 2×SSC (SSC=0.15M NaCl, 0.015M sodium citrate) hybridisation buffer at 37°, as previously described (27). Washes were performed in 2×SSC/0.1% w/v sodium dodecyl sulphate (SDS) at 42–55°. The signal from one duplicating plaque persisted following 55° washes. The DNA from this plaque contained an inset of 2.5 kb (HEK 2.5) was labeled with $\alpha^{32}$P-ATP (as above) and used to rescreen the random primed LK63 cDNA ligrary in 2×SSC hybridization buffer at 65°. Thirty two duplicating positives were isolated and screened by hybridization with a degenerate oligonucleotide based on the N terminal oligonucleotide was chosen for complete characterisation.

DNA Sequencing and Analysis of HEK cDNA

HEK 4.5 was subcloned into pGEM7 which had been digested with EcoRI and treated with calf intestinal phosphatase. Double stranded DNA was purified on a caesium chloride gradient and used as the template in dideoxy chain termination sequence reactions (29). Sense and antisense oligonucleotide primers were used to complete sequencing with T7 DNA polymerase (Promega). Protein sequence alignment was performed using the GAP programme (University of Wisconsin, Genetics Computer Group).

Expression of HEK in COS Cells

The HEK 4.5 EcoRI insert was blunt ended with Klenow DNA polymerase 1 and dATP plus dTTP, followed by ligation to BstXI adaptors. The adapted insert was ligated to BstXI digested CDM8 (30). Sense and antisense constructs were prepared and transfected into COS cells using DEAE-dextran/chloroquine with dimethyl sulphoxide (DMSO) (17). Two days post-transfection, COS cells were stained with IIIA4 followed by fluorescein isothiocyanate conjugated (FITC)-conjugated sheep anti-mouse immunoglobulin (Ig) (Silenus) and examined under a fluorescence microscope.

Northern and Southern Blot Analysis of Cell Lines

Poly A+ selected mRNA was isolated as previously described (31) and fractionated on a 1% formaldehyde agarose gel prior to transfer onto a HybondC extra membrane (Amersham). Filters were probed with HEK 4.5 and subsequently with a glyceraldehyde-3-phosphate dehydrogenase (GAPDH) insert as a control. DNA was prepared by lysis with guanidine hydrochloride (32), transferred to Zetaprobe membranes and hybridised under conditions suggested by the manufacturer (Bio-Rad). In order to minimise cross hybridisation with other tyrosine kinases in Southern analysis of genomic DNA, PCR was used to generate a 1.1 kb HEK probe which spans a less highly conserved region of the molecule (nucleotides 1,109 to 2,241, FIG. 1). The autoradiogram of the Southern blot was digitised using the MacScan programme on a Macintosh IIx computer.

Scatchard Analysis of IIIA4 Binding to Cell Lines

Binding of $^{125}$I labelled IIIA4 to cell lines was performed in competition with unlabelled IIIA4 as previously described (33).

Protein Analysis

The HEK protein was subjected to hydrophobicity analysis as described by Kyte and Doolittle (40). The results are shown in FIG. 9.

Oligos to Construct Expression Vectors Encoding Variants of the Extracellular Domain of HEK Primer HEK5'/92 has the following sequence:

```
      Bam Hl Eco Rl
      ┌────┐ ┌────┐
      GTAGGGATCCGAATTCTGCACCAGCAACATG   (SEQ ID NO: 6)
                    └───────────────┘
```

The BamnH1 and Eco R1 sites are indicated above the sequence and the underlined portion corresponds to positions 86 to 102 of the sequence set forth in FIG. 1.

Primer HEK/EE14/92 has the sequence:

```
        Bam Hl
        ┌────┐
      GTAGGGATCCTACACTTGGCTACTTTCA    (SEQ ID NO: 7)
              └┘ └──────────────┘
              Stop  Codon
```

The underlined portion after the stop codon is the reversed and complemented sequence of nucleotide 1710–1725 of FIG. 1.

```
        Bam Hl
        ┌────┐
      GCGGATCCTTGCCTACTTTCACCA    (SEQ ID NO: 8)
              └──────────────┘
```

The underlined sequence when reversed and complemented corresponds to 1708–1723 of the sequence in FIG. 1 and does not contain the stop codon permitting read through from the BamH1 site.

PCR Conditions

PCR was performed with Taq polymerase under standard conditions using CsCl purified pGEM7-HEK, which contains the full length HEK cDNA, as a template. Cycle times and temperatures:

60' at 97° C.

60' at 55° C.

90' at 73° C.

the reaction was carried out for ten cycles.

1. The 1.7 kb PCR product of the HEK5'/92 and HEK/EE14/92 was purified using Geneclean, digested with Eco R1 and BamH1 and cloned between the Eco R1 and Bcl I site of pEE14 (obtained from Celltech, Berkshire, UK). Analysis showed the predicted 1.7 kb insert in the clones which were designated "pEE14-HEK".

2. The 1.7 kb PCR product of 5' HEk5'/92 and HEK/TAG/3' was digested with BamH1, cloned into BglII site of AP-Tag-1, Flanagan & Leder (39). Using SnaB1, the sense of the clones could be determined to fused clones with the correct orientation. The resulting clones were designated AP-TAG-HEK.

Expression pEE14-HEK was transfected into CHO cells and lines selected with methionine sulfoxime.

AP-TAG-HEK was transfected into 3T3 cells with pSV2 neo and clones selected with G418.

EXAMPLE 2. HEK

Isolation and Characterisation of cDNA Clones for HEK

One duplicating signal was obtained from screening approximately 250,000 plaques of an LK63-derived λgt10 cDNA library under relaxed conditions with a degenerate 51 mer oligonucleotide. This plaque contained a 2.5 kb insert (HEK2.5) which hyoridised with a single 5.5–6.0 kb mRNA species in Northern blot analysis of cell lines expressing HEK i.e. LK63 and JM. PCR using HEK 2.5 and oligonucleotide primers based on conserved motifs within the catalytic domains of tyrosine kinases (28), gave DNA products of the appropriate size. These results indicated HEK 2.5 was trunucated at the 5' end. HEK 2.5 was used to re-screen the library under more stringent conditions and a 4.5 kb HEK (HEK 4.5) clone isolated. This clone hybridised with a degenerate oligonucleotide based on the N terminal protein sequence and produced DNA bands of the predicted sizes in PCR reactions using the primers referred to above. These data indicated the 4.5 kb clone probably contained the complete HEK coding region.

The sequence of the coding region for HEK together with partial 3' and 5' untranslated sequence, is shown in FIG. 1. An open reading frame of 2,952 nucleotides extends from the initiation methionine at position 10 o the first termination codon 3051. Translation of the cDNA results in a predicted protein of 983 amino acids (AAs). There is identity between the AAs obtained by sequencing of purified HEK protein and the predicted AA product of the cDNA clone (see FIG. 1). The predicted molecular weight of the translated protein (minus the putative signal peptide) is 92.8 kD. This is in good agreement with previous results demonstrating a core protein of approximately 95 kD in both unicamycin- and endoglycosidase-treated LK63 cells (25). The predicted protein product of the HEK cDNA don has the features of a type 1 a integral membrane protein (35). Two predominantly hydrophobic regions indiciate a putative signal peptide (AAs 1–20) and a transmembrane segment (AAs 542–565). The extracellular domain of 521 AAs contains five possible sites for N linked glycosylation. The N terminal region (AAs 21–376) of the extracellular domain is rich in cysteine residues. The C-terminal region (AAs 326–511) of the extracellular domain contains two repeats homologous to those found in fibronectin type III (36). The cytoplasmic domain (AAs 566–983) of HEK contains a typical ATP binding site (GXGXXG) (SEQ ID NO: 12) at AA positions 628–633 and a putative autophosphorylation site (E/DXXYXX) (SEQ ID NOS: 13–14) at position 779.

Protein sequence alignment shows a high degree of homology between HEK and eph, elk, eck, eek and erk in the catalytic domains. HEK has the following overall protein sequence homology with each of the three sequenced members of the eph RTK family: (chicken) CEK 56.4%, (rat) elk 56.1%; (rat) eck 50.6%; (human) eph 42.3%. Protein sequence alignment between HEK and a close relative ELK is shown in FIG. 2. The homology between these molecules is greatest within the catalytic domains. Outside the catalytic domains, numerous short motifs which may be of structural or functional significance, are conserved between HEK, eph, elk and eck, particularly towards the N terminus. There is strict conservation of the number and spatial arrangement of cysteine residues within the extracellular domains of HEY, eph, elk and eck (34). These cytokine residues cluster within the N terminal portion of the extracellular domains (36). The C terminal regions of the extracellular domains contain repeats which are homologous to those found in fibronectin type III (36). HEK has a cysteine in the C terminal tail (AA928), rather than the tyrosine which is conserved in this position between other members of the EPH/ELK family. This may be of significance in that phosphorylation of C terminal tyrosine residues can regulate tyrosine kinase activity (37). However HEK has a C terminal tyrosine at position 937, which also appears to be in a better context for autophosphorylation (38).

Transfection and Expression of HEK in COS Cells

To demonstrate that the cDNA clone isolated did indeed encode the molecule recognised by the IIIA4 Mab, HEK 4.5 was subcloned into the expression vector CDM8 and transfected into COS cells in both sense and antisense orientations. As shown in FIG. 3, COS cells transfected with HEK in the sense orientation stained specifically with IIIA4, confirming that the cDNA clone contains the full coding sequence and is identical to the molecule recognised by IIIA4. COS cells transfected with HEK in the antisense orientation did not stain with IIIA4.

Expression of HEK in Human Lymphoid Cell Lines

Cell surface staining with IIIA4 revealed a highly restricted pattern of HEK expression on LK63—a pre B cell line, and JM—a T cell line. To further explore the expression of HEK, Northern blot analysis was performed with HEK 4.5 (FIGS. 4 to 6). A single 5.5–6.0 kb band was seen in both LK63 and JM cells. However there was a less intense band of the same size in another T cell line—HSB-2—which did not stain with IIIA4. Other cell lines in which HEK transcripts were detected include Lila-1, MOIT4 and HeLa. There were no HEK transcripts detected in a range of other cell lines although a weak band was seen in heart muscle (FIG. 6). The number of HEK molecules was determined on HSB-2, LK63/CD20+ and other cells using Scatchard analysis of IIIA4 MAb binding. The LK63/CD20+ cells had approximately 15,000 sites per cell and JM cells had 9,500 sites per cell. In contrast, HSB-2 had approximately 1,070 sites per cell, which is too low for detection by immunofluorescence against the autofluorescence background of this cell line. The affinity constants for antibody binding were in the range of $2.5-4.0 \times 10^9$. Raji and K562 cells showed no detectable antibody binding above background. Tables 1 and 2 summarise the phenotype of HEK expression cell lines.

Southern Blot Analysis

To investigate the basis for overexpression of HEK in the lymphoid tumour cell line LK63, Southern analysis of genomic DNA was performed (FIG. 7). A 1.1 kb fragment covering a less conserved region of HEK (see above), was used as a probe in order to minimise background arising from conserved regions of the catalytic domains of related tyrosine kinase molecules. Compared with normal peripheral blood mononuclear cell DNA, there is no apparent amplification or rearrangement of the HEK gene in the LK63 or LK63/CD20+ tumour cell lines.

Chromosomal Assignment of HEK

HEK cDNA was used as a probe to locate the position of the HEK gene within the normal human chromosome complement. Chromosomal assignment was performed in two ways—by in situ hybridisation and by Southern analysis of somatic cell hybrids. Thirty normal male metaphases were examined for a fluorescent signal: Twenty four of these metaphases showed signal on one or both chromatids of chromosome 3 in the region of 3cen→3p12.1. 85% of this signal was at 3p11.2 (FIG. 8). There were a total of nine non-specific background dots observed in these 30 metaphases. Similar results were obtained from the hybridisation to the second male. Southern blot analysis of the hybrid cell panel showed hybridisation of the HEK probe only to hybrids containing material from human chromosome 3. Bands of 5.2, 4.8, 4.3, 2.4 and 1.9 kb were obtained from the Hind III digest and bands of 4.3, 3.2 and 1.9kb were obtained from the Taq1 digest. The hybrid cell panel used represents the entire human genome except for chromosomes 2, 6q, 8, 11p and Y. The results from both techniques thus localised the HEK gene to chromosome 3 and in situ hybridisation analysis positioned this more precisely to 3p11.2. This region was not cytogenetically abnormal in HEK-positive tumours. Similarly, there was no isolated change in the copy number of chromosome 3 in HEK-positive cell lines and no isochromosome formation involving chromosome 3.

TABLE 1 Phenotype of HEK-positive Human Lymphoid Cell Lines

The phenotype of HEK-positive cell lines was determined by staining for T and B cell markers followed by FACS analysis. + weakly positive, ++ positive, +++ strongly positive.

|       | HLA4 | IgM | CD19 | CD20 | CD1 | CD2 | CD3 | CD4 | CD7 | CD8 |
|-------|------|-----|------|------|-----|-----|-----|-----|-----|-----|
| LK63  | ++   | +   | +    | -    | -   | -   | -   | -   | -   | -   |
| LK63T | +++  | ++  | ++   | ++   | -   | -   | -   | -   | -   | -   |
| Lila-1| -    | +   | ++   | -    | -   | -   | -   | -   | -   | -   |
| HSB-2 | -    | -   | -    | -    | -   | -   | +   | -   | ++  | -   |
| JM    | +    | -   | -    | -    | +   | -   | +   | ++  | ++  | ++  |
| Molt4 | -    | -   | -    | -    | +   | ++  | -   | -   | ++  | +   |

TABLE 2

Summary of HEK expression in human cell lines HEK-positive cell lines were characterised using a combination of cell surface staining, Northern blot analysis and Scatchard analysis.
+ weakly positive, + + positive,
+ + + strongly positive. NT, not tested.

| Line   | Lineage  | BLA4/IF | Receptors/cell | RNA   |
|--------|----------|---------|----------------|-------|
| LK63   | Pre-B    | + +     | 15,000         | + +   |
| LK63T  | Pre-B    | + + +   | NT             | + + + |
| Lila   | Pre-B    | -       | NT             | +     |
| JM     | T cell   | ++      | 9,500          | ++    |
| HSB-2  | T cell   | -       | 1,100          | +     |
| Molt 4 | T cell   | -       | NT             | +     |
| HeLa   | Cervical | -       | NT             | +     |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Ullrich, A. and Schlessigner, *J. Cell* 61; 203–212,1990.
2. Carpenter, G., & Cohen, S. *J. Biol. Chem.* 265, 7709–7712, 1990.
3. Williams, L. T. *Science* 243, 1564–1570, 1989.
4. Yeung, Y. G., Jubinsky, P. T., Sengupta, A, Yeung, D. C. Y., & Stanley, E. R. *Proc. Natl. Acad. Sci. USA* 84, 1268–1271, 1987.
5. Hanks, S. K., Quinn, A. M. and Hunter, T. *Science* 241: 42–52,1988.
6. Yarden, Y. and Ullrich, A. *Ann. Rev. Biochem.* 51: 443–478,1988.
7. Yarden, Y., Kuang, W. J., Yang-Feng, T., Coussens, L., Munemitsu, S., Dull, T. J., Chen, E., Schlessinger, J., Francke, U. & Ullrich, A. *EMBO J.* 6. 3341–3351, 1987.
8. Chabot, B., Stephenson, D. A., Chapman, V. M., Besner, P and Verstein, A. *Nature* 335: 88–89, 1988.
9. Geissler, E. M., Ryan, M. A. and Housman, E. E. *Cell* 55: 185–192,1988.
10. Nocka, K., Majunder, S., Chabot, B., Rya, P., Cervone, M., Bertstein, A., and Besmer, P. *Genes Dev.* 3: 816–826, 1989.
11. Williams, D. E., Eisenman, J., Barid, A., Ranch, C., vanNess, K., March, C. J., Park, L. S., Martin, U., Mochinzuki, D. Y., Boswell, H. S., Burgess, G. S., Cosman, D. and Lyman, S. D., *Cell* 63: 167–174,1990.
12. Zsebo, K. M., Williams, D. A., Geissler, E. N., Broudy, V. C., Martin, F. H., Atkins, H. L., Hsu, R. Y., Burkett, N. C., Okino, K. H., Langly, K. E., Smith, K. A., Takeishi, T., Cattanach, B. M., Galli, S. J. and Suggs, S. V. *Cell* 63: 213–244, 1990.
13. Huang, E., Nocka, K., Beier, D. R., Chui, T. Y., Buck, J., Lahn, H. W., Wellner, D., Leder, P. and Besner, P. *Cell* 63: 225–233, 1990.
14. Copeland, N. G. Gilbert, D. J., Cho, B. C., Donovan, P. J., Jenkins, N. A., Cosman, D., Anderson, D., Lyman, S. D. and Williams, D. E. *Cell* 63: 175–183, 1990.
15. Bennett, D. *J. Morphol.* 98: 199–233,1956.
16. Bishop, J. M. *Ann. Rev. Biochem.* 52: 301–354, 1983.
17. Hunter, T. and Cooper, J. A. *Ann. Rev. Biochem.* 54: 897–930,1985.
18. Resh, M. *Oncogenes:* 1437–1444, 1990.
19. Eiseman, E. and Bolen, J. B. *Cancer Cells* 2: 303–310, 1990.
20. Veiliette, A., Bookman, M. A., Horak, E. M. and Bolen, J. B. *Cell* 55: 301–308, 1988.
21. Rudd, C. E., Tevillyan, J. M., Dasgupta, J. D., Wong, L. L. and Schlossman, S. F. *Proc. Natl. Acad. Sci. USA* 85: 5190–5194, 1988.
22. Hirai, H., Maru, Y., Hagiwara, K., Nishida, J. and Talaku, F. *Science* 238: 1717–1720, 1987.
23. Lindberg, R. A. and Hunter, T. *Mol. Cell. Biol.* 10: 6316–6324,1990.
24. Salvaris, E., Novotny, J. R., Welch, K., Campbell, L. & Boyd, A. W. *Leukemia Research* (in press).

25. Boyd, A. W., Ward, L. D., Wicks, I. P., Simpson, R. L., Salvaris, E., Wilks, A., Welch, K., Loudovaris, M., Rockman, S. & Busmanis, I. *J. Biol. Chem.* 267 (5): 3262–3267, 1992.
26. Martin, F. H., Castro, M. M., Aboul-ela, F. & Tinoco, I. *Nucleic Acids Res.* 13: 8927, 1985.
27. Gearing, D. P., Gough, N. M., King, J. A., Hilton, D. J., Nicola, N. A., Simpson, R. J., Nice, E. C., Kelso, A. & Metcalf, D. *EMBO J.* 6, 3995–4002, 1987.
28. Wilks, A. *Proc. Natl. Acad. Sci. USA* 86: 1603–1607, 1988.
29. Sanger, F., Nicklen, S. and Coulson, A. R. *Proc. Natl. Acad. Sci. USA* 74: 5463–5467, 1977.
30. Seed, B. & Aruffo, A. *Proc. Natl. Acad. Sci. USA* 84, 3365–3369, 1987.
31. van Driel, I., Wilks, A. F., Pietersz, G. A. & Goding, J. W. *Proc. Natl. Acad. Sci. USA* 82: 8619–8623, 1985.
32. Bowtell, D. D. Anal. *Biochem.* 162: 463–465. 1987.
33. Trucco, M., & de Petris, S. in *Immunological Methods,* eds. Lefkovits, I., & Pernis, B. (Academic Press, New York, N.Y.) Vol 2, pp 1–26.
34. Lhotak, V., Greer, P., Letwin, K. & Pawson, T. *Mol. Cell. Biol.* 11: 2496–2502, 1991.
35. Singer, S. J., in *Annu. Rev. Cell. Biol.* eds Palade, G. E. Alberts, B. M. and Spudich, J. A. (Annual Reviews Inc. Palo Alto, Calif.), Vol 6: 247–296, 1990.
36. Pasquale, E. B. *Cell Regulation* 2: 523–534, 1991.
37. Cantley, L. C., Auger, K. R., Carpenter, C., Duckworth, B., Graziani, A., Kapellar, R. and Soltoff, S. *Cell* 64, 281–302, 1991.
38. Pearson, R. B., and Kemp, B. E. in Methods in Enzymology, eds. Hunter, T., and Seffon, B. M. (Academic Press, San Diego, LA) Vol 200 p62–81, 1991.
39. Flanagan and Leder *Cell* 63: 185–194, 1990.
40. Kyte and Doolittle *J. Mol. Biol.* 157: 105–132; 1982.

What is claimed is:

1. A method of screening for a soluble ligand to a receptor-type tyrosine kinase comprising the amino acid sequence consisting of SEQ ID NO:1, said method comprising contacting a sample to be tested with a cell line that expresses said tyrosine kinase and screening for phosphorylation in said cell line.

2. The method according to claim 1 wherein the cell line is LK 63 or a HEK transformant cell line, wherein said HEK protein has a molecular weight of 120–150 KD.

3. The method according to claim 1 or 2 wherein the sample is a supernatant fluid.

4. A method of screening for a soluble ligand to a receptor-type tyrosine kinase comprising the amino acid sequence consisting of SEQ ID NO:1, which is recognized by monoclonal antibody IIIA4, said method comprising passing the sample through an affinity column having said tyrosine kinase immobilized thereon and purifying said soluble ligand bound to said receptor-type tyrosine kinase.

5. A method of screening for a soluble ligand to a receptor-type tyrosine kinase comprising the amino acid sequence consisting of SEQ ID NO:1, which is recognized by IIIA4 antibody, said method comprising contacting a sample to be tested with a cell line that expresses said tyrosine kinase and screening for phosphorylation in said cell line.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Glu Leu Ile Pro Gln Pro
1               5
```

(2) INFORMATION FOR SEQ ID NO:2:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

```
Glu Leu Ile Pro Gln Pro Ser Asn Glu Val Asn Leu Xaa Asp
1               5                   10
```

(2) INFORMATION FOR SEQ ID NO:3:

(i) SEQUENCE CHARACTERISTICS:
      (A) LENGTH: 19 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:3:

```
Glu Leu Ile Pro Gln Pro Ser Asn Glu Val Asn Leu Xaa Asp Ser Lys
1               5                   10                  15
```

```
Xaa Ile Gln (2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Gly Tyr Arg Leu Pro Pro Pro Met Asp Cys Pro Ala Ala Leu Tyr Gln
1               5                   10                  15

Leu Met Leu Asp Cys
            20

(2) INFORMATION FOR SEQ ID NO:5:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 6..7
        (D) OTHER INFORMATION: /mod_base= i (ix) FEATURE:
        (A) NAME/KEY: modified_base
        (B) LOCATION: 9..10
        (D) OTHER INFORMATION: /mod_base= i (ix) FEATURE:
        (A) NAME/KEY: modified_base
        (B) LOCATION: 12..13
        (D) OTHER INFORMATION: /mod_base= i (ix) FEATURE:
        (A) NAME/KEY: modified_base
        (B) LOCATION: 15..16
        (D) OTHER INFORMATION: /mod_base= i (ix) FEATURE:
        (A) NAME/KEY: modified_base
        (B) LOCATION: 18..19
        (D) OTHER INFORMATION: /mod_base= i (ix) FEATURE:
        (A) NAME/KEY: modified_base
        (B) LOCATION: 30..31
        (D) OTHER INFORMATION: /mod_base= i (ix) FEATURE:
        (A) NAME/KEY: modified_base
        (B) LOCATION: 33..34
        (D) OTHER INFORMATION: /mod_base= i (ix) FEATURE:
        (A) NAME/KEY: modified_base
        (B) LOCATION: 36..37
        (D) OTHER INFORMATION: /mod_base= i (ix) FEATURE:
        (A) NAME/KEY: modified_base
        (B) LOCATION: 39..40
        (D) OTHER INFORMATION: /mod_base= i (ix) FEATURE:
```

(A) NAME/KEY: modified_base
        (B) LOCATION: 48..49
        (D) OTHER INFORMATION: /mod_base= i (xi) SEQUENCE DESCRIPTION: SEQ ID NO:5:

TACCGNCTNC CNCCNCCNAT GGACTGCCCN GCNGCNCTNT ACCAACTNAT G        51

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTAGGGATCC GAATTCTGCA CCAGCAACAT G                              31

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GTAGGGATCC TACACTTGGC TACTTTCA                                  28

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GCGGATCCTT GCCTACTTTC ACCA                                      24

(2) INFORMATION FOR SEQ ID NO:9:

(i) SEQUENCE CHARACTERISTICS:
        (A) LENGTH: 3132 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 100..3048

(xi) SEQUENCE DESCRIPTION: SEQ ID NO:9:

CATGGATGGT AACTTCTCCA GCAATCAGAG CGCTCCCCCT CACATCAGTG GCATGCTTCA        60

TGGAGATATG CTCCTCTCAC TGCCCTCTGC ACCAGCAAC ATG GAT TGT CAG CTC         114
                                           Met Asp Cys Gln Leu
                                            1               5

TCC ATC CTC CTC CTT CTC AGC TGC TCT GTT CTC GAC AGC TTC GGG GAA        162
Ser Ile Leu Leu Leu Leu Ser Cys Ser Val Leu Asp Ser Phe Gly Glu
         10                  15                  20

```
CTG ATT CCG CAG CCT TCC AAT GAA GTC AAT CTA CTG GAT TCA AAA ACA      210
Leu Ile Pro Gln Pro Ser Asn Glu Val Asn Leu Leu Asp Ser Lys Thr
            25                  30                  35

ATT CAA GGG GAG CTG GGC TGG ATC TCT TAT CCA TCA CAT GGG TGG GAA      258
Ile Gln Gly Glu Leu Gly Trp Ile Ser Tyr Pro Ser His Gly Trp Glu
        40                  45                  50

GAG ATC AGT GGT GTG GAT GAA CAT TAC ACA CCC ATC AGG ACT TAC CAG      306
Glu Ile Ser Gly Val Asp Glu His Tyr Thr Pro Ile Arg Thr Tyr Gln
    55                  60                  65

GTG TGC AAT GTC ATG GAC CAC AGT CAA AAC AAT TGG CTG AGA ACA AAC      354
Val Cys Asn Val Met Asp His Ser Gln Asn Asn Trp Leu Arg Thr Asn
70                  75                  80                  85

TGG GTC CCC AGG AAC TCA GCT CAG AAG ATT TAT GTG GAG CTC AAG TTC      402
Trp Val Pro Arg Asn Ser Ala Gln Lys Ile Tyr Val Glu Leu Lys Phe
                90                  95                 100

ACT CTA CGA GAC TGC AAT AGC ATT CCA TTG GTT TTA GGA ACT TGC AAG      450
Thr Leu Arg Asp Cys Asn Ser Ile Pro Leu Val Leu Gly Thr Cys Lys
            105                 110                 115

GAG ACA TTC AAC CTG TAC TAC ATG GAG TCT GAT GAT GAT CAT GGG GTG      498
Glu Thr Phe Asn Leu Tyr Tyr Met Glu Ser Asp Asp Asp His Gly Val
        120                 125                 130

AAA TTT CGA GAG CAT CAG TTT ACA AAG ATT GAC ACC ATT GCA GCT GAT      546
Lys Phe Arg Glu His Gln Phe Thr Lys Ile Asp Thr Ile Ala Ala Asp
    135                 140                 145

GAA AGT TTC ACT CAA ATG GAT CTT GGG GAC CGT ATT CTG AAG CTC AAC      594
Glu Ser Phe Thr Gln Met Asp Leu Gly Asp Arg Ile Leu Lys Leu Asn
150                 155                 160                 165

ACT GAG ATT AGA GAA GTA GGT CCT GTC AAC AAG AAG GGA TTT TAT TTG      642
Thr Glu Ile Arg Glu Val Gly Pro Val Asn Lys Lys Gly Phe Tyr Leu
                170                 175                 180

GCA TTT CAA GAT GTT GGT GCT TGT GTT GCC TTG GTG TCT GTG AGA GTA      690
Ala Phe Gln Asp Val Gly Ala Cys Val Ala Leu Val Ser Val Arg Val
            185                 190                 195

TAC TTC AAA AAG TGC CCA TTT ACA GTG AAG AAT CTG GCT ATG TTT CCA      738
Tyr Phe Lys Lys Cys Pro Phe Thr Val Lys Asn Leu Ala Met Phe Pro
        200                 205                 210

GAC ACG GTA CCC ATG GAC TCC CAG TCC CTG GTG GAG GTT AGA GGG TCT      786
Asp Thr Val Pro Met Asp Ser Gln Ser Leu Val Glu Val Arg Gly Ser
    215                 220                 225

TGT GTC AAC AAT TCT AAG GAG GAA GAT CCT CCA AGG ATG TAC TGC AGT      834
Cys Val Asn Asn Ser Lys Glu Glu Asp Pro Pro Arg Met Tyr Cys Ser
230                 235                 240                 245

ACA GAA GGC GAA TGG CTT GTA CCC ATT GGC AAG TGT TCC TGC AAT GCT      882
Thr Glu Gly Glu Trp Leu Val Pro Ile Gly Lys Cys Ser Cys Asn Ala
                250                 255                 260

GGC TAT GAA GAA AGA GGT TTT ATG TGC CAA GCT TGT CGA CCA GGT TTC      930
Gly Tyr Glu Glu Arg Gly Phe Met Cys Gln Ala Cys Arg Pro Gly Phe
            265                 270                 275

TAC AAG GCA TTG GAT GGT AAT ATG AAG TGT GCT AAG TGC CCG CCT CAC      978
Tyr Lys Ala Leu Asp Gly Asn Met Lys Cys Ala Lys Cys Pro Pro His
        280                 285                 290

AGT TCT ACT CAG GAA GAT GGT TCA ATG AAC TGC AGG TGT GAG AAT AAT     1026
Ser Ser Thr Gln Glu Asp Gly Ser Met Asn Cys Arg Cys Glu Asn Asn
    295                 300                 305

TAC TTC CGG GCA GAC AAA GAC CCT CCA TCC ATG GCT TGT ACC CGA CCT     1074
Tyr Phe Arg Ala Asp Lys Asp Pro Pro Ser Met Ala Cys Thr Arg Pro
310                 315                 320                 325

CCA TCT TCA CCA AGA AAT GTT ATC TCT AAT ATA AAC GAG ACC TCA GTT     1122
Pro Ser Ser Pro Arg Asn Val Ile Ser Asn Ile Asn Glu Thr Ser Val
```

-continued

```
                     330                    335                      340
ATC CTG GAC TGG AGT TGG CCC CTG GAC ACA GGA GGC CGG AAA GAT GTT     1170
Ile Leu Asp Trp Ser Trp Pro Leu Asp Thr Gly Gly Arg Lys Asp Val
                 345                 350                355

ACC TTC AAC ATC ATA TGT AAA AAA TGT GGG TGG AAT ATA AAA CAG TGT     1218
Thr Phe Asn Ile Ile Cys Lys Lys Cys Gly Trp Asn Ile Lys Gln Cys
             360                 365                 370

GAG CCA TGC AGC CCA AAT GTC CGC TTC CTC CCT CGA CAG TTT GGA CTC     1266
Glu Pro Cys Ser Pro Asn Val Arg Phe Leu Pro Arg Gln Phe Gly Leu
        375                 380                 385

ACC AAC ACC ACG GTG ACA GTG ACA GAC CTT CTG GCA CAT ACT AAC TAC     1314
Thr Asn Thr Thr Val Thr Val Thr Asp Leu Leu Ala His Thr Asn Tyr
390                 395                 400                 405

ACC TTT GAG ATT GAT GCC GTT AAT GGG GTG TCA GAG CTG AGC TCC CCA     1362
Thr Phe Glu Ile Asp Ala Val Asn Gly Val Ser Glu Leu Ser Ser Pro
                410                 415                 420

CCA AGA CAG TTT GCT GCG GTC AGC ATC ACA ACT AAT CAG GCT GCT CCA     1410
Pro Arg Gln Phe Ala Ala Val Ser Ile Thr Thr Asn Gln Ala Ala Pro
            425                 430                 435

TCA CCT GTC CTG ACG ATT AAG AAA GAT CGG ACC TCC AGA AAT AGC ATC     1458
Ser Pro Val Leu Thr Ile Lys Lys Asp Arg Thr Ser Arg Asn Ser Ile
        440                 445                 450

TCT TTG TCC TGG CAA GAA CCT GAA CAT CCT AAT GGG ATC ATA TTG GAC     1506
Ser Leu Ser Trp Gln Glu Pro Glu His Pro Asn Gly Ile Ile Leu Asp
455                 460                 465

TAC GAG GTC AAA TAC TAT GAA AAG CAG GAA CAA GAA ACA AGT TAT ACC     1554
Tyr Glu Val Lys Tyr Tyr Glu Lys Gln Glu Gln Glu Thr Ser Tyr Thr
470                 475                 480                 485

ATT CTG AGG GCA AGA GGC ACA AAT GTT ACC ATC AGT AGC CTC AAG CCT     1602
Ile Leu Arg Ala Arg Gly Thr Asn Val Thr Ile Ser Ser Leu Lys Pro
                490                 495                 500

GAC ACT ATA TAC GTA TTA CAA ATC CGA GCC CGA ACA GCC GCT GGA TAT     1650
Asp Thr Ile Tyr Val Leu Gln Ile Arg Ala Arg Thr Ala Ala Gly Tyr
            505                 510                 515

GGG ACG AAC AGC CGC AAG TTT GAG TTT GAA ACT AGT CCA GAC TCT TTC     1698
Gly Thr Asn Ser Arg Lys Phe Glu Phe Glu Thr Ser Pro Asp Ser Phe
        520                 525                 530

TCC ATC TCT GGT GAA AGT AGC CAA GTG GTC ATG ATC GCC ATT TCA GCG     1746
Ser Ile Ser Gly Glu Ser Ser Gln Val Val Met Ile Ala Ile Ser Ala
    535                 540                 545

GCA GTA GCA ATT ATT CTC CTC ACT GTT GTC ATC TAT GTT TTG ATT GGG     1794
Ala Val Ala Ile Ile Leu Leu Thr Val Val Ile Tyr Val Leu Ile Gly
550                 555                 560                 565

AGG TTC TGT GGC TAT AAG TCA AAA CAT GGG GCA GAT GAA AAA AGA CTT     1842
Arg Phe Cys Gly Tyr Lys Ser Lys His Gly Ala Asp Glu Lys Arg Leu
                570                 575                 580

CAT TTT GGC AAT GGG CAT TTA AAA CTT CCA GGT CTC AGG ACT TAT GTT     1890
His Phe Gly Asn Gly His Leu Lys Leu Pro Gly Leu Arg Thr Tyr Val
            585                 590                 595

GAC CCA CAT ACA TAT GAA GAC CCT ACC CAA GCT GTT CAT GAG TTT GCC     1938
Asp Pro His Thr Tyr Glu Asp Pro Thr Gln Ala Val His Glu Phe Ala
        600                 605                 610

AAG GAA TTG GAT GCC ACC AAC ATA TCC ATT GAT AAA GTT GTT GGA GCA     1986
Lys Glu Leu Asp Ala Thr Asn Ile Ser Ile Asp Lys Val Val Gly Ala
    615                 620                 625

GGT GAA TTT GGA GAG GTG TGC AGT GGT CGC TTA AAA CTT CCT TCA AAA     2034
Gly Glu Phe Gly Glu Val Cys Ser Gly Arg Leu Lys Leu Pro Ser Lys
630                 635                 640                 645

AAA GAG ATT TCA GTG GCC ATT AAA ACC CTG AAA GTT GGC TAC ACA GAA     2082
```

-continued

```
                Lys Glu Ile Ser Val Ala Ile Lys Thr Leu Lys Val Gly Tyr Thr Glu
                            650                 655                 660

AAG CAG AGG AGA GAC TTC CTG GGA GAA GCA AGC ATT ATG GGA CAG TTT        2130
Lys Gln Arg Arg Asp Phe Leu Gly Glu Ala Ser Ile Met Gly Gln Phe
            665                 670                 675

GAC CAC CCC AAT ATC ATT CGA CTG GAA GGA GTT GTT ACC AAA AGT AAG        2178
Asp His Pro Asn Ile Ile Arg Leu Glu Gly Val Val Thr Lys Ser Lys
        680                 685                 690

CCA GTT ATG ATT GTC ACA GAA TAC ATG GAG AAT GGT TCC TTG GAT AGT        2226
Pro Val Met Ile Val Thr Glu Tyr Met Glu Asn Gly Ser Leu Asp Ser
    695                 700                 705

TTC CTA CGT AAA CAC GAT GCC CAG TTT ACT GTC ATT CAG CTA CTG GGG        2274
Phe Leu Arg Lys His Asp Ala Gln Phe Thr Val Ile Gln Leu Leu Gly
710                 715                 720                 725

ATG CTT CGA GGG ATA GCA TCT GGC ATG AAG TAC CTG TCA GAC ATG GGC        2322
Met Leu Arg Gly Ile Ala Ser Gly Met Lys Tyr Leu Ser Asp Met Gly
                730                 735                 740

TAT GTT CAC CGA GAC CTC GCT GCT CGG AAC ATC TTG ATC AAC AGT AAC        2370
Tyr Val His Arg Asp Leu Ala Ala Arg Asn Ile Leu Ile Asn Ser Asn
            745                 750                 755

TTG GTG TGT AAG GTT TCT GAT TTC GGA CTT TCG CGT GTC CTG GAG GAT        2418
Leu Val Cys Lys Val Ser Asp Phe Gly Leu Ser Arg Val Leu Glu Asp
        760                 765                 770

GAC CCA GAA GCT GCT TAT ACA ACA AGA GGA GGG AAG ATC CCA ATC AGG        2466
Asp Pro Glu Ala Ala Tyr Thr Thr Arg Gly Gly Lys Ile Pro Ile Arg
    775                 780                 785

TGG ACA TCA CCA GAA GCT ATA GCC TAC CGC AAG TTC ACG TCA GCC AGC        2514
Trp Thr Ser Pro Glu Ala Ile Ala Tyr Arg Lys Phe Thr Ser Ala Ser
790                 795                 800                 805

GAT GTA TGG AGT TAT GGG ATT GTT CTC TGG GAG GTG ATG TCT TAT GGA        2562
Asp Val Trp Ser Tyr Gly Ile Val Leu Trp Glu Val Met Ser Tyr Gly
                810                 815                 820

GAG AGA CCA TAC TGG GAG ATG TCC AAT CAG GAT GTA ATT AAA GCT GTA        2610
Glu Arg Pro Tyr Trp Glu Met Ser Asn Gln Asp Val Ile Lys Ala Val
            825                 830                 835

GAT GAG GGC TAT CGA CTG CCA CCC CCC ATG GAC TGC CCA GCT GCC TTG        2658
Asp Glu Gly Tyr Arg Leu Pro Pro Pro Met Asp Cys Pro Ala Ala Leu
        840                 845                 850

TAT CAG CTG ATG CTG GAC TGC TGG CAG AAA GAC AGG AAC AAC AGA CCC        2706
Tyr Gln Leu Met Leu Asp Cys Trp Gln Lys Asp Arg Asn Asn Arg Pro
    855                 860                 865

AAG TTT GAG CAG ATT GTT AGT ATT CTG GAC AAG CTT ATC CGG AAT CCC        2754
Lys Phe Glu Gln Ile Val Ser Ile Leu Asp Lys Leu Ile Arg Asn Pro
870                 875                 880                 885

GGC AGC CTG AAG ATC ATC ACC AGT GCA GCC GCA AGG CCA TCA AAC CTT        2802
Gly Ser Leu Lys Ile Ile Thr Ser Ala Ala Ala Arg Pro Ser Asn Leu
                890                 895                 900

CTT CTG GAC CAA AGC AAT GTG GAT ATC TCT ACC TTC CGC ACA ACA GGT        2850
Leu Leu Asp Gln Ser Asn Val Asp Ile Ser Thr Phe Arg Thr Thr Gly
            905                 910                 915

GAC TGG CTT AAT GGT GTC CGG ACA GCA CAC TGC AAG GAA ATC TTC ACG        2898
Asp Trp Leu Asn Gly Val Arg Thr Ala His Cys Lys Glu Ile Phe Thr
        920                 925                 930

GGC GTG GAG TAC AGT TCT TGT GAC ACA ATA GCC AAG ATT TCC ACA GAT        2946
Gly Val Glu Tyr Ser Ser Cys Asp Thr Ile Ala Lys Ile Ser Thr Asp
    935                 940                 945

GAC ATG AAA AAG GTT GGT GTC ACC GTG GTT GGG CCA CAG AAG AAG ATC        2994
Asp Met Lys Lys Val Gly Val Thr Val Val Gly Pro Gln Lys Lys Ile
950                 955                 960                 965
```

```
ATC AGT AGC ATT AAA GCT CTA GAA ACG CAA TCA AAG AAT GGC CCA GTT       3042
Ile Ser Ser Ile Lys Ala Leu Glu Thr Gln Ser Lys Asn Gly Pro Val
                970                 975                 980

CCC GTG TAAAGCACGA CGGAAGTGCT TCTGGACGGA AGTGGTGGCT GTGGAAGGCG        3098
Pro Val
TCAAGTCATC CTGCAGACAG ACAATAATTC TGGA                                 3132
```

(2) INFORMATION FOR SEQ ID NO:10:

(i) SEQUENCE CHARACTERISTICS:
        (A) LENGTH: 983 amino acids
        (B) TYPE: amino acid
        (D) TOPOLOGY: linear (ii) MOLECULE TYPE: protein (xi) SEQUENCE DESCRIPTION: SEQ ID NO:10:

```
Met Asp Cys Gln Leu Ser Ile Leu Leu Leu Ser Cys Ser Val Leu
 1               5                  10                  15

Asp Ser Phe Gly Glu Leu Ile Pro Gln Pro Ser Asn Glu Val Asn Leu
                20                  25                  30

Leu Asp Ser Lys Thr Ile Gln Gly Glu Leu Gly Trp Ile Ser Tyr Pro
         35                  40                  45

Ser His Gly Trp Glu Glu Ile Ser Gly Val Asp Glu His Tyr Thr Pro
     50                  55                  60

Ile Arg Thr Tyr Gln Val Cys Asn Val Met Asp His Ser Gln Asn Asn
 65              70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
            100                 105                 110

Leu Gly Thr Cys Lys Glu Thr Phe Asn Leu Tyr Tyr Met Glu Ser Asp
         115                 120                 125

Asp Asp His Gly Val Lys Phe Arg Glu His Gln Phe Thr Lys Ile Asp
     130                 135                 140

Thr Ile Ala Ala Asp Glu Ser Phe Thr Gln Met Asp Leu Gly Asp Arg
145                 150                 155                 160

Ile Leu Lys Leu Asn Thr Glu Ile Arg Glu Val Gly Pro Val Asn Lys
                165                 170                 175

Lys Gly Phe Tyr Leu Ala Phe Gln Asp Val Gly Ala Cys Val Ala Leu
            180                 185                 190

Val Ser Val Arg Val Tyr Phe Lys Lys Cys Pro Phe Thr Val Lys Asn
        195                 200                 205

Leu Ala Met Phe Pro Asp Thr Val Pro Met Asp Ser Gln Ser Leu Val
    210                 215                 220

Glu Val Arg Gly Ser Cys Val Asn Asn Ser Lys Glu Glu Asp Pro Pro
225                 230                 235                 240

Arg Met Tyr Cys Ser Thr Glu Gly Glu Trp Leu Val Pro Ile Gly Lys
                245                 250                 255

Cys Ser Cys Asn Ala Gly Tyr Glu Glu Arg Gly Phe Met Cys Gln Ala
            260                 265                 270

Cys Arg Pro Gly Phe Tyr Lys Ala Leu Asp Gly Asn Met Lys Cys Ala
        275                 280                 285

Lys Cys Pro Pro His Ser Ser Thr Gln Glu Asp Gly Ser Met Asn Cys
    290                 295                 300

Arg Cys Glu Asn Asn Tyr Phe Arg Ala Asp Lys Asp Pro Pro Ser Met
305                 310                 315                 320
```

-continued

```
Ala Cys Thr Arg Pro Ser Ser Pro Arg Asn Val Ile Ser Asn Ile
            325                 330                 335

Asn Glu Thr Ser Val Ile Leu Asp Trp Ser Trp Pro Leu Asp Thr Gly
            340                 345                 350

Gly Arg Lys Asp Val Thr Phe Asn Ile Ile Cys Lys Lys Cys Gly Trp
            355                 360                 365

Asn Ile Lys Gln Cys Glu Pro Cys Ser Pro Asn Val Arg Phe Leu Pro
        370                 375                 380

Arg Gln Phe Gly Leu Thr Asn Thr Thr Val Thr Val Thr Asp Leu Leu
385                 390                 395                 400

Ala His Thr Asn Tyr Thr Phe Glu Ile Asp Ala Val Asn Gly Val Ser
            405                 410                 415

Glu Leu Ser Ser Pro Pro Arg Gln Phe Ala Ala Val Ser Ile Thr Thr
            420                 425                 430

Asn Gln Ala Ala Pro Ser Pro Val Leu Thr Ile Lys Lys Asp Arg Thr
            435                 440                 445

Ser Arg Asn Ser Ile Ser Leu Ser Trp Gln Glu Pro Glu His Pro Asn
            450                 455                 460

Gly Ile Ile Leu Asp Tyr Glu Val Lys Tyr Tyr Glu Lys Gln Glu Gln
465                 470                 475                 480

Glu Thr Ser Tyr Thr Ile Leu Arg Ala Arg Gly Thr Asn Val Thr Ile
            485                 490                 495

Ser Ser Leu Lys Pro Asp Thr Ile Tyr Val Leu Gln Ile Arg Ala Arg
            500                 505                 510

Thr Ala Ala Gly Tyr Gly Thr Asn Ser Arg Lys Phe Glu Phe Glu Thr
            515                 520                 525

Ser Pro Asp Ser Phe Ser Ile Ser Gly Glu Ser Ser Gln Val Val Met
            530                 535                 540

Ile Ala Ile Ser Ala Ala Val Ala Ile Ile Leu Leu Thr Val Val Ile
545                 550                 555                 560

Tyr Val Leu Ile Gly Arg Phe Cys Gly Tyr Lys Ser Lys His Gly Ala
            565                 570                 575

Asp Glu Lys Arg Leu His Phe Gly Asn Gly His Leu Lys Leu Pro Gly
            580                 585                 590

Leu Arg Thr Tyr Val Asp Pro His Thr Tyr Glu Asp Pro Thr Gln Ala
            595                 600                 605

Val His Glu Phe Ala Lys Glu Leu Asp Ala Thr Asn Ile Ser Ile Asp
            610                 615                 620

Lys Val Val Gly Ala Gly Glu Phe Gly Glu Val Cys Ser Gly Arg Leu
625                 630                 635                 640

Lys Leu Pro Ser Lys Lys Glu Ile Ser Val Ala Ile Lys Thr Leu Lys
            645                 650                 655

Val Gly Tyr Thr Glu Lys Gln Arg Arg Asp Phe Leu Gly Glu Ala Ser
            660                 665                 670

Ile Met Gly Gln Phe Asp His Pro Asn Ile Ile Arg Leu Glu Gly Val
            675                 680                 685

Val Thr Lys Ser Lys Pro Val Met Ile Val Thr Glu Tyr Met Glu Asn
            690                 695                 700

Gly Ser Leu Asp Ser Phe Leu Arg Lys His Asp Ala Gln Phe Thr Val
705                 710                 715                 720

Ile Gln Leu Leu Gly Met Leu Arg Gly Ile Ala Ser Gly Met Lys Tyr
            725                 730                 735
```

```
Leu Ser Asp Met Gly Tyr Val His Arg Asp Leu Ala Ala Arg Asn Ile
            740                 745                 750

Leu Ile Asn Ser Asn Leu Val Cys Lys Val Ser Asp Phe Gly Leu Ser
            755                 760                 765

Arg Val Leu Glu Asp Asp Pro Glu Ala Ala Tyr Thr Thr Arg Gly Gly
            770                 775                 780

Lys Ile Pro Ile Arg Trp Thr Ser Pro Glu Ala Ile Ala Tyr Arg Lys
785                 790                 795                 800

Phe Thr Ser Ala Ser Asp Val Trp Ser Tyr Gly Ile Val Leu Trp Glu
                805                 810                 815

Val Met Ser Tyr Gly Glu Arg Pro Tyr Trp Glu Met Ser Asn Gln Asp
            820                 825                 830

Val Ile Lys Ala Val Asp Glu Gly Tyr Arg Leu Pro Pro Pro Met Asp
            835                 840                 845

Cys Pro Ala Ala Leu Tyr Gln Leu Met Leu Asp Cys Trp Gln Lys Asp
            850                 855                 860

Arg Asn Asn Arg Pro Lys Phe Glu Gln Ile Val Ser Ile Leu Asp Lys
865                 870                 875                 880

Leu Ile Arg Asn Pro Gly Ser Leu Lys Ile Ile Thr Ser Ala Ala Ala
                885                 890                 895

Arg Pro Ser Asn Leu Leu Leu Asp Gln Ser Asn Val Asp Ile Ser Thr
            900                 905                 910

Phe Arg Thr Thr Gly Asp Trp Leu Asn Gly Val Arg Thr Ala His Cys
            915                 920                 925

Lys Glu Ile Phe Thr Gly Val Glu Tyr Ser Ser Cys Asp Thr Ile Ala
            930                 935                 940

Lys Ile Ser Thr Asp Asp Met Lys Lys Val Gly Val Thr Val Val Gly
945                 950                 955                 960

Pro Gln Lys Lys Ile Ile Ser Ser Ile Lys Ala Leu Glu Thr Gln Ser
                965                 970                 975

Lys Asn Gly Pro Val Pro Val
            980

(2) INFORMATION FOR SEQ ID NO:11:

(i) SEQUENCE CHARACTERISTICS:
        (A) LENGTH: 432 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Met Ala Leu Leu Phe Leu Ala Ala Val Ala Ala Met Glu Thr Met Thr
1               5                   10                  15

Arg Ala Thr Ala Thr Ala Asn Ala Ser Val Tyr Tyr Thr Ser Val Ile
            20                  25                  30

Ala Thr Lys Ser Ala Phe Trp Ser Ala Pro Tyr Leu Val Ser Val Phe
            35                  40                  45

Gly Leu Met Val Val Ser Phe Leu Thr Arg Ala Glu Val Val Ile Lys
        50                  55                  60

Leu Asn Gly Asp Met Arg Thr Lys Pro Asn Ser Val Ala Lys Pro Ala
65                  70                  75                  80

Thr Phe Ser Gln Glu Ala Glu Gly Ser His Ser Asn Asn Leu Asn Thr
                85                  90                  95
```

```
Phe Glu Pro Asn Leu Thr Phe Ile Asn Arg Gly His Arg Thr Met Arg
                100                 105                 110

Val Ser Leu Asn Pro Ser Asn Tyr Met Ser Leu Phe Ser Ile Gln Phe
            115                 120                 125

Val Glu Met Thr Gly Ala Glu Thr Ile Ala Thr Ile Pro Arg Ser Pro
        130                 135                 140

Ser Glu Ala Pro Ile Thr Arg Thr Gly Tyr Phe Glu Val Ser Val Gly
145                 150                 155                 160

Ile Val Ile Glu His Pro Arg Glu Asp Tyr Arg Ala Asp Arg Arg Ser
                165                 170                 175

Ser Arg Asp Asp Glu Val Leu Glu Cys Arg Ser Ile Ser Ser Trp Pro
            180                 185                 190

Asp Gln Ile Ile Arg Glu His Asn Phe Asn Ser Ser Met Ala Ser Gln
        195                 200                 205

Thr Asn Thr Ala Arg Asp Gly Arg Gly Met Val Val Val Val Lys Phe
    210                 215                 220

Gly Met Cys Gln Leu Thr Asp Asp Tyr Lys Met Lys Ile Ile Phe Asn
225                 230                 235                 240

Glu Arg Ile Val Ser Phe Val Lys Glu Glu Ile Tyr Lys Gly Arg Tyr
                245                 250                 255

Ser Lys Pro Phe Pro His Val Ser Asn Thr Pro Ile Met His Gln Val
            260                 265                 270

Ser Ala Thr Met Arg Thr Pro Gln Gln Glu Leu Arg Glu Leu Pro Leu
        275                 280                 285

Gly Ala Gly Val Val Phe Val Val Ser Leu Ala Ser Ile Val Cys Ser
290                 295                 300

Lys Arg Ala Ser Lys Glu Ala Val Tyr Ser Asp Leu Gln Tyr Ser Thr
305                 310                 315                 320

Arg Gly Ser Ala Ser Ser Arg Ile Phe Ala Gln Asn Gly Ala Glu Asn
                325                 330                 335

Val Tyr Gln Thr Asn Ile Glu Gln Asp His Ser Arg Ala Glu Asn Thr
            340                 345                 350

Met Ala Ser Glu Leu Leu Arg Ile Leu Ala His Leu His Ser Met Arg
        355                 360                 365

Val Met Asn Gln Ser Ser Val Met Ala Ser Asp Pro Thr Ser Ser Leu
    370                 375                 380

Val Ala Met Phe Asp Thr Val Ala Thr Ile Thr Val Gln Pro Arg Ile
385                 390                 395                 400

Pro Phe Thr Ala Thr Val Asp Ser Ala Ile Lys Met Val Gln Tyr Arg
                405                 410                 415

Asp Ser Leu Thr Ala Gly Phe Thr Leu Gln Leu Val Thr Gln Met Thr
            420                 425                 430

(2) INFORMATION FOR SEQ ID NO:12:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

Gly Xaa Gly Xaa Xaa Gly
1               5
```

(2) INFORMATION FOR SEQ ID NO:13:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

Glu Xaa Xaa Tyr Xaa Xaa
1               5

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

Asp Xaa Xaa Tyr Xaa Xaa
1               5